(12) United States Patent
Igarashi et al.

(10) Patent No.: US 7,282,041 B2
(45) Date of Patent: Oct. 16, 2007

(54) MULTI LUMEN CATHETER

(75) Inventors: Junichi Igarashi, Osaka (JP); Katsuhiro Hiejima, Osaka (JP)

(73) Assignee: Nipro Corporation, Osaka (JP)

( * ) Notice: Subject to any disclaimer, the term of this patent is extended or adjusted under 35 U.S.C. 154(b) by 668 days.

(21) Appl. No.: 10/606,374

(22) Filed: Jun. 26, 2003

(65) Prior Publication Data
US 2005/0177094 A1    Aug. 11, 2005

(30) Foreign Application Priority Data

| Jun. 27, 2002 | (JP) | ............................. 2002-187145 |
| Nov. 29, 2002 | (JP) | ............................. 2002-346852 |
| Dec. 6, 2002  | (JP) | ............................. 2002-354671 |
| Jan. 28, 2003 | (JP) | ............................. 2003-019141 |

(51) Int. Cl.
*A61M 3/00*    (2006.01)
(52) U.S. Cl. ....................................................... 604/43
(58) Field of Classification Search ................. 604/43, 604/93.01, 96.01, 264, 40, 164.01, 533, 4.01, 604/101.04, 84, 171
See application file for complete search history.

(56) References Cited

U.S. PATENT DOCUMENTS

| 2,148,541 | A | * | 2/1939 | Dierker ........................ 604/40 |
| 4,180,068 | A |   | 12/1979 | Jacobsen et al. ......... 128/214 R |
| 5,149,330 | A |   | 9/1992 | Brightbill .................... 604/280 |
| 6,190,371 | B1 | * | 2/2001 | Maginot et al. ............. 604/523 |

FOREIGN PATENT DOCUMENTS

| JP | 09-253215 A | 9/1997 |
| JP | 2001-137350 A | 5/2001 |
| WO | 97/35629 | 10/1997 |

* cited by examiner

*Primary Examiner*—Nicholas D. Lucchesi
*Assistant Examiner*—Christopher D. Koharski
(74) *Attorney, Agent, or Firm*—Kubovcik & Kubovcik

(57) ABSTRACT

A multi lumen catheter including an inner tube having a front tip, an outer tube, a tube or lumen for inserting a guide wire, a blood extraction lumen and a blood return lumen which are formed in the outer tube and inner tube, respectively, or both in the outer tube, wherein the inner tube is inserted in the outer tube, and allowed to slide relative thereto, and the front tip is jointed to the front end of the outer tube to shut off communication of the lumens with the exterior. A multi-lumen catheter with balloon includes a balloon provided on a tabular body at a front end thereof, a blood return port and a blood extraction port provided in the tubular body on opposite sides of the balloon, and an outer cylinder slidable on the tubular body to close the blood extraction and blood return ports and the balloon.

23 Claims, 20 Drawing Sheets (a)

(b)

(c)

(a) partial enlarged view (b) cross sectional view (a) partial enlarged view

(12) at inflation
(12) at shrinkage (b) cross sectional view

MULTI LUMEN CATHETER

This application claims priority of Japanese patent application Nos. 2002-187145 filed Jun. 27, 2002; 2002-346852 filed Nov. 25, 2002; 2002-354671 filed Dec. 6, 2002; and 2003-019141 filed Jan. 28, 2003.

BACKGROUND OF THE INVENTION

This invention relates to a multi lumen catheter used for dialysis therapy such as emergency hemodialysis, and to a multi lumen catheter with a balloon.

PRIOR ART

In an emergency hemodialysis, there is used a multi lumen catheter having a blood extraction lumen, a blood return lumen and a lumen for inserting a guide wire (Japanese Patent No. 2832722, Japanese Patent No. 3124807, JP-A-6-339529 et al.). The catheter is often indwelled in a blood vessel even after the dialysis has been finished. In this case, a thrombus is formed due to the blood remaining in a blood extraction lumen and in a blood return lumen so as to cause such problems that the lumens are occluded and the blood poorly flows.

In order to solve this problem, therefore, a treatment called "heparin locking" is conducted to fill the blood extraction lumen and the blood return lumen with heparin when the catheter is indewelled in a blood vessel before conducting the dialysis. However, even when heparin locking is conducted, the lumens have a blood extraction port and a blood return port that are open in the blood vessel, and there remains a probability in that the blood enters into the lumens through the blood extraction port and the blood return port to form a thrombus.

In order to reliably maintain the heparin locking and prevent the formation of thrombus, there has been proposed a catheter equipped with, as means for closing the blood extraction port and the blood return port, a mechanism capable of opening and closing the blood extraction port or the blood return port by covering the catheter with a sheath having ports at positions corresponding to the blood extraction port and the blood return port, and by turning the sheath (JP-A-9-253214 and 9-253215). With this catheter, the blood extraction port formed in the side surface of the catheter is brought into a position corresponding to the port formed in the sheath, and the dialysis is conducted in a state where the blood extraction port is opened. After the dialysis has been finished, the blood extraction lumen and the blood return lumen are filled with heparin, and the sheath is turned relative to the catheter such that the blood extraction port is not in the position corresponding to the port in the sheath. Thus, the blood extraction port is closed by the sheath, and heparin locking is reliably maintained in the blood extraction lumen.

In this catheter, however, the blood return lumen is also used as a lumen for inserting the guide wire, and the blood return lumen has a blood return port opening facing the front end side at the front end. Therefore, the blood return port cannot be closed by turning the sheath. Accordingly, reliable heparin locking is not accomplished in the blood return lumen, and there is a probability that thrombi may be formed due to the invasion of blood as with the conventional catheters.

There has further been developed a catheter having a structure capable of closing both the blood extraction port and the blood return port (JP-A-2001-137350). This catheter has a structure in which a blood extraction lumen, a blood return lumen and a lumen for inserting a guide wire are separately provided, the blood extraction port and the blood return port being provided in a side surface of the catheter, and the catheter is covered with a sheath having ports at positions corresponding to the blood extraction port and to the blood return port. In this catheter, the blood extraction port and the blood return port are both closed by turning or sliding the sheath. Therefore, heparin locking is reliably maintained in both the blood extraction lumen and the blood return lumen.

However, this catheter is covered with a sheath and has a diameter greater than that of a conventional catheter without the sheath, and a patient must bear an increased burden in using it. If the catheter is designed to possess a diameter equal to that of conventional catheters, then, the flow rate through the blood extraction lumen and/or the blood return lumen decreases to affect the dialysis treatment.

Besides, the catheter covered with the sheath must maintain liquid tightness in the gap between the sheath and the catheter. Otherwise, the blood enters into the gap to form thrombi and makes it difficult to turn or slide the sheath. It is very difficult to maintain the liquid tightness in the gap between the sheath and the catheter all the time that the catheter is indwelled in the body.

SUMMARY OF THE INVENTION

In view of the above-mentioned circumstances, it is an object of this invention to provide a multi lumen catheter capable of reliably maintaining heparin locking without increasing the diameter of the catheter yet maintaining a flow rate comparable to that of conventional catheters, and without the need of maintaining liquid tightness in the gap between a sheath and the catheter.

The present invention is a multi lumen catheter comprising an inner tube having a front tip, an outer tube, a tube or lumen for inserting a guide wire, a blood extraction lumen and a blood return lumen which are formed in the outer tube and the inner tube, respectively, or both in the outer tube, wherein the inner tube is inserted in the outer tube, and allowed to slide relative to the outer tube, and the front tip can be jointed to the front end of the outer tube to shut off the communication of the blood extraction lumen and the blood return lumen from the exterior of the catheter.

The present invention is a multi lumen catheter having the following constitution (A) or (B);

(A) a multi lumen catheter 1 comprising:

an outer tube 2 having an inner cavity constituting a blood extraction lumen 21, and a blood extraction port 22 which is open at an end facing the front end side of the catheter in the axial direction and provides communication between said blood extraction lumen 21 and the exterior of the catheter 1;

an inner tube 3 having an inner cavity constituting a blood return lumen 31 and a blood return port 32 for providing communication between said blood return lumen 31 and the exterior of the catheter 1; and a tube 4 for inserting a guide wire and having an inner cavity constituting a lumen 41 for inserting the guide wire, and a front tip 42 of a tapered shape; and (B) a multi lumen catheter 1 comprising:

an outer tube 2 having an inner cavity constituting a blood extraction lumen 21 and a blood return lumen 31, a blood extraction port 22 which is open toward the front end side of the catheter in the axial direction and provides communication between said blood extraction lumen 21 and the exterior of the catheter 1, and a blood return port 32 open toward the front end side of the catheter in the axial direction on the front side of said blood extraction port 22 and provides communication between said blood return lumen 31 and the exterior of the catheter 1; and an inner tube 4 having an inner cavity constituting a lumen 41 for inserting a guide wire and a front tip 42 of a tapered shape;

wherein said inner tube 4 is inserted in said outer tube 2, and is allowed to slide relative to said outer tube 2, and the front tip 42 is joined to the front end of said outer tube 4 to shut off the communication of said blood extraction lumen 21 and said blood return lumen 31 from the exterior of the catheter 1.

The present invention is further a multi lumen catheter (C) with balloon comprising:

a base end portion (51);

a slender flexible tubular main body (52) extending from the base end portion (51) to a front end portion;

a front tip (53) having an outer shape tapered toward the front end which is provided at a front end of the tubular main body (52);

a balloon (12) being provided on an outer side of the tubular main body (52) at a portion close to the front tip side (53) but on the side of the base end portion (51), and having an outer diameter, when it is deflated, smaller than a maximum outer diameter of the front tip (53);

either one of a blood return port (81) of a blood return lumen (13) and a blood extraction port (71) of a blood extraction lumen (14) being formed in the tubular main body (52) on the front tip (53) side in front of the balloon (12) and the other one being formed in the tubular main body (52) on the base end portion (51) side at the back of the balloon (12); and an outer tube (50) being provided on the outermost side of said tubular main body (52) so as to slide in the lengthwise direction of said body (52), wherein the blood extraction port (71), the blood return port (81) and a balloon-mounting portion are closed when the end of the outer tube (50) comes in contact with the front tip (53).

DETAILED DESCRIPTION OF THE INVENTION

Catheter (A)

Figure 1:
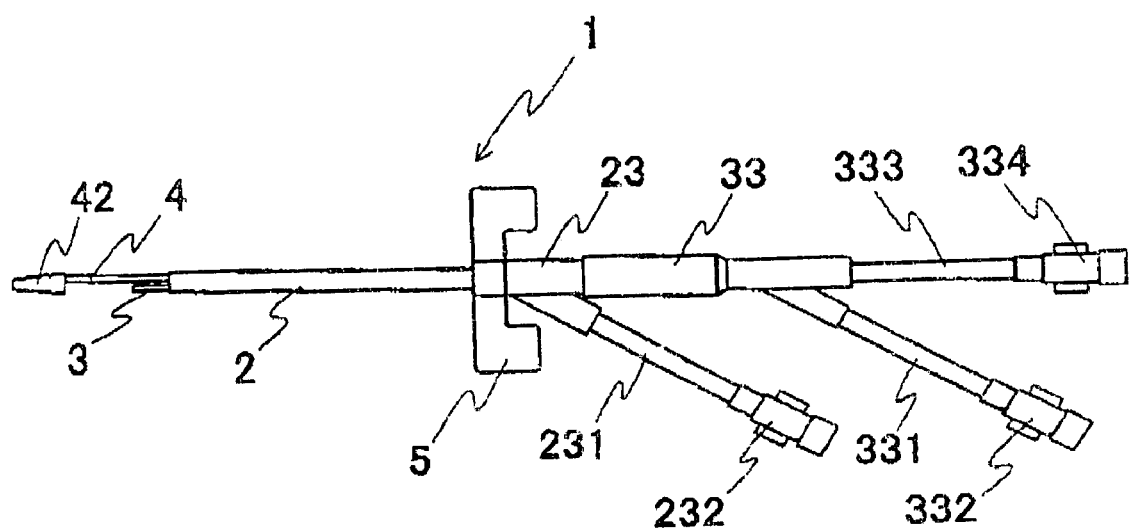
FIG. 1 is a side view of a first embodiment of a multi lumen catheter (A) of the invention in a state where dialysis is being conducted.

One of the embodiments of the present invention is a multi lumen catheter (A) comprising an outer tube 2 having an inner cavity constituting a blood extraction lumen 21 and a blood extraction port 22 which is open at an end facing the front end side in the axial direction and provides communication between said blood extraction lumen 21 and the exterior of the catheter 1;

an inner tube 3 having an inner cavity constituting a blood return lumen 31 and a blood return port 32 for providing communication between said blood return lumen 31 and the exterior of the catheter 1; and a tube 4 for inserting a guide wire and having an inner cavity constituting a lumen 41 for inserting the guide wire, and a front tip 42 of a tapered shape;

wherein said inner tube 3 is at least partly secured (at its proximal end) to said tube 4 for inserting the guide wire, said inner tube 3 and said tube 4 for inserting the guide wire are inserted in said outer tube 2, which are allowed to slide relative to said outer tube 2, and, when said outer tube 2, said inner tube 3 and said tube 4 for inserting the guide wire are in such an order that the front tip 42, the blood return port 32 and the blood extraction port 22 are successively arranged in order from the front end side, the blood extraction lumen 21 with the blood extraction port 22 and the blood return lumen 31 with the blood return port 32 communicate with the exterior of the catheter 1, and when the front tip 42 of said tube 4 for inserting the guide wire is joined to the front end of said outer tube 2, the communication of said blood extraction lumen 21 and said blood return lumen 31 with the exterior of the catheter 1 is shut off.

Mode of Operation

The multi-lumen catheter (A) of the present invention has a structure in which the outer tube constitutes a blood extraction lumen in the inside while performing the function of a sheath, and in this blood extraction lumen are inserted the inner tube that constitutes the blood return lumen and the tube for inserting the guide wire that constitutes the lumen for inserting the guide wire. This constitution makes it possible to provide a catheter having the advantages of a catheter equipped with a sheath without increasing the diameter of the catheter as with conventional catheters. Therefore, the multi-lumen catheter of the invention possesses the above constitution with a diameter comparable to that of the conventional catheters, which does not cause increased pain to a patient and does not decrease the flow rate through the blood extraction lumen and the blood return lumen.

In the multi-lumen catheter (A) of the invention, further, the blood extraction port and the blood return port are closed when the front tip of the tube for inserting the guide wire is joined to the outer tube and, hence, no gap exists between the catheter and a sheath. This eliminates the need for designing a structure for maintaining liquid tightness in a gap between a sheath and the catheter unlike a conventional catheter.

Multi-lumen catheter (A) of the invention will now be described in detail with reference to embodiments shown in FIGS. 1-9 of the accompanying drawings. However, the invention is in no way limited to these embodiments.

Figure 2:
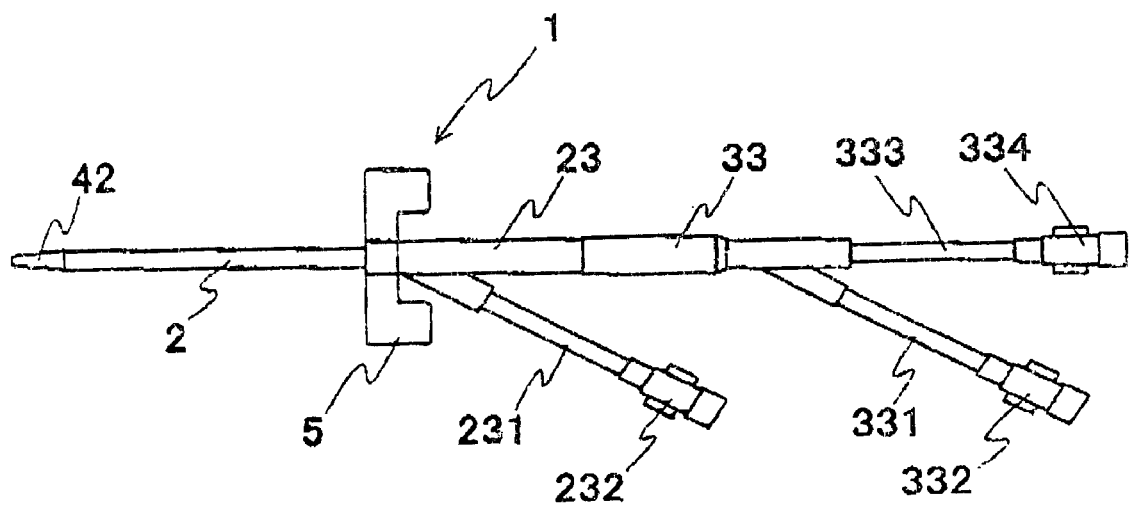
FIG. 2 is a side view of the multi lumen catheter of FIG. 1 in a state where dialysis is not being conducted.
Figure 3:
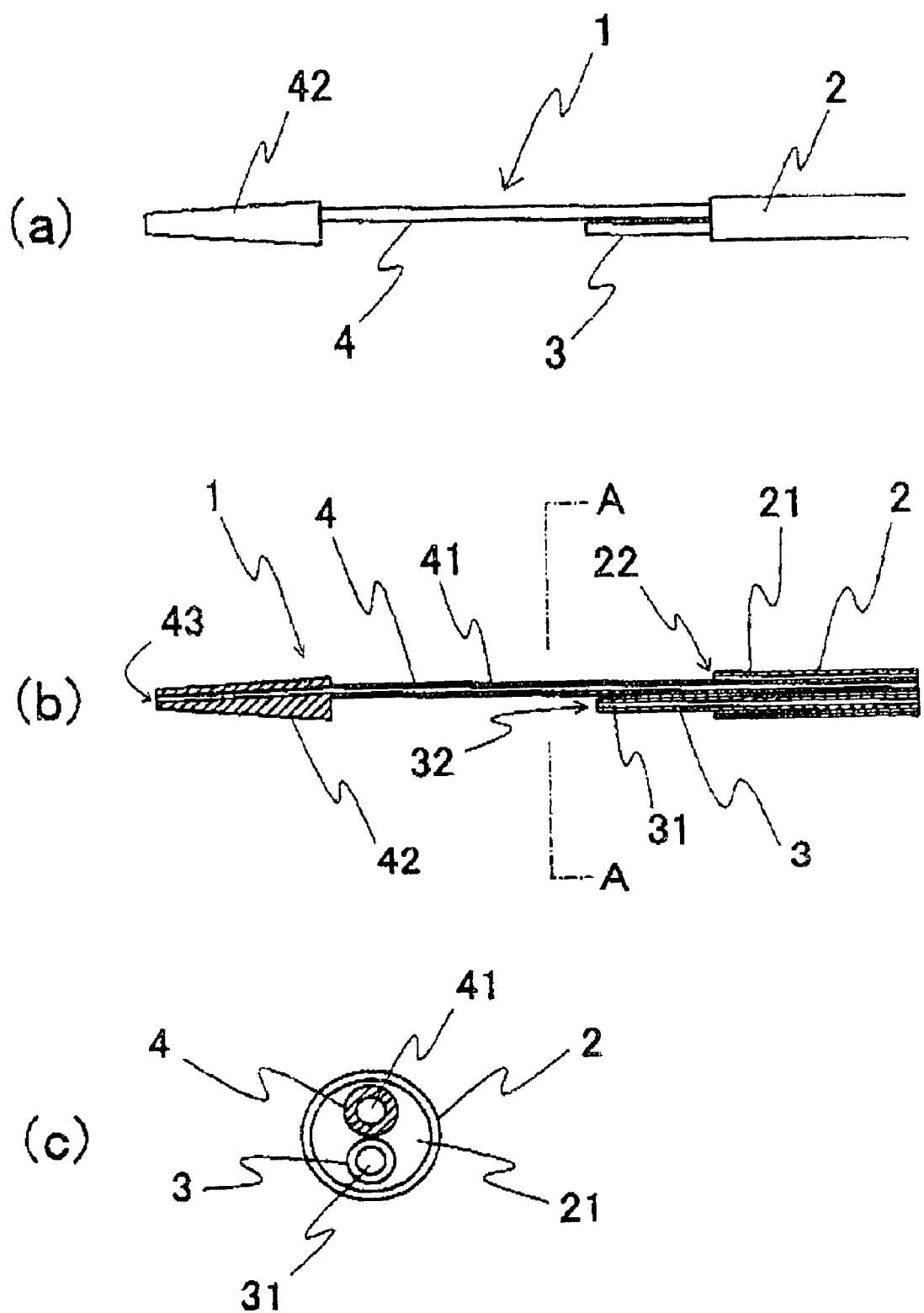
FIGS. 3(a), (b) and (c) are views illustrating, on an enlarged scale, the front end of the multi lumen catheter of FIG. 1.
Figure 4:
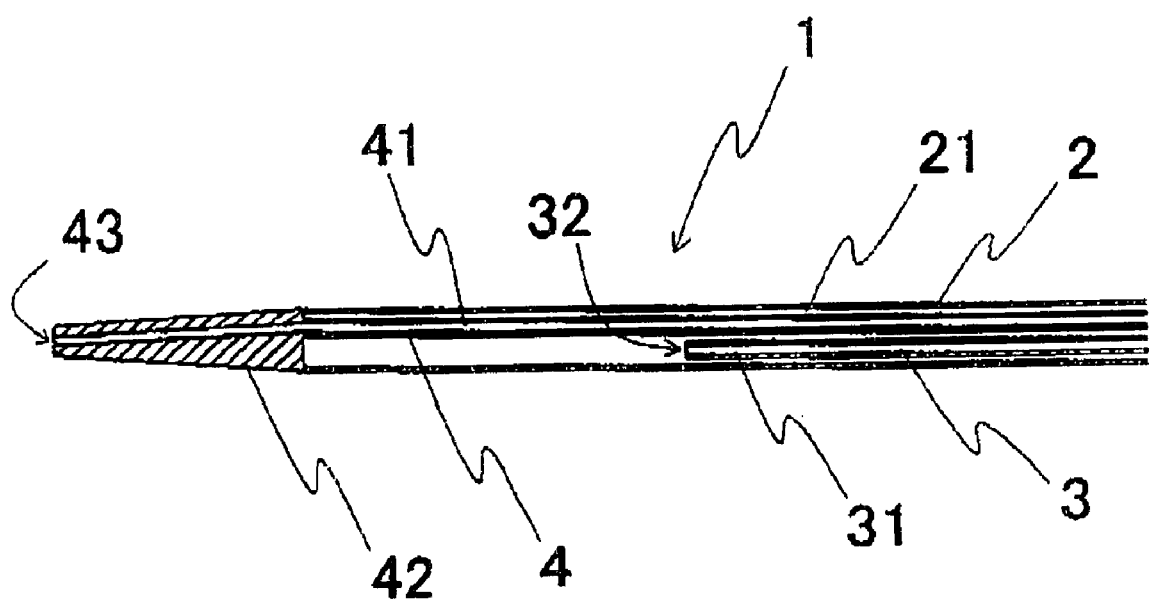
FIG. 4 is a view illustrating, on an enlarged scale, the front end of the multi lumen catheter of FIG. 2.
Figure 5:
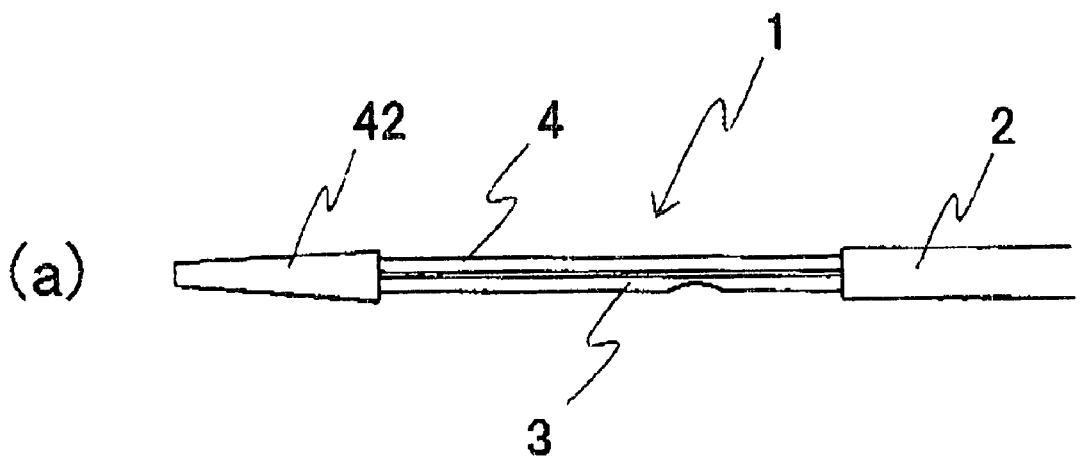
FIGS. 5(a), (b) and (c) are views illustrating, on an enlarged scale, the front end of the multi lumen catheter (A) of the invention according to a second embodiment.
Figure 5:
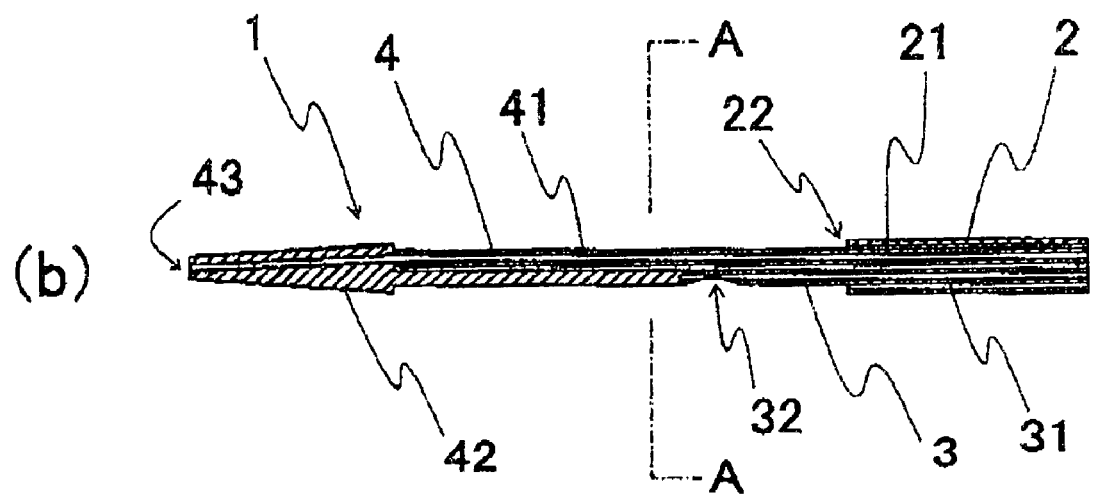
Figure 5:
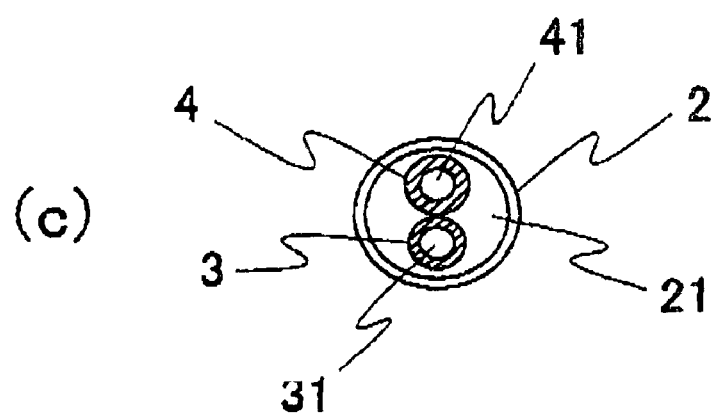
Figure 6:
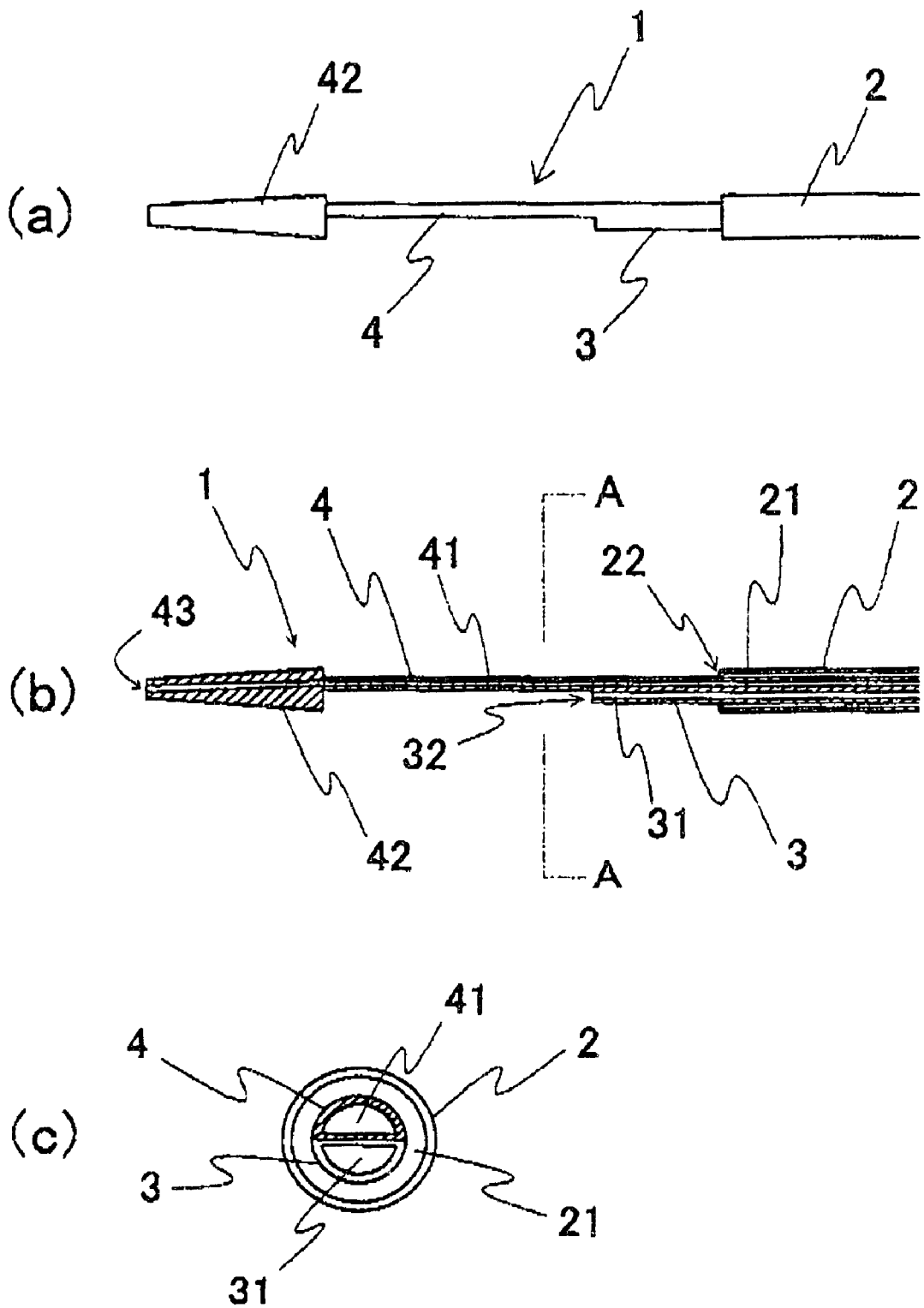
FIGS. 6(a), (b) and (c) are views illustrating, on an enlarged scale, the front end of the multi lumen catheter (A) of the invention according to a third embodiment.
Figure 7:
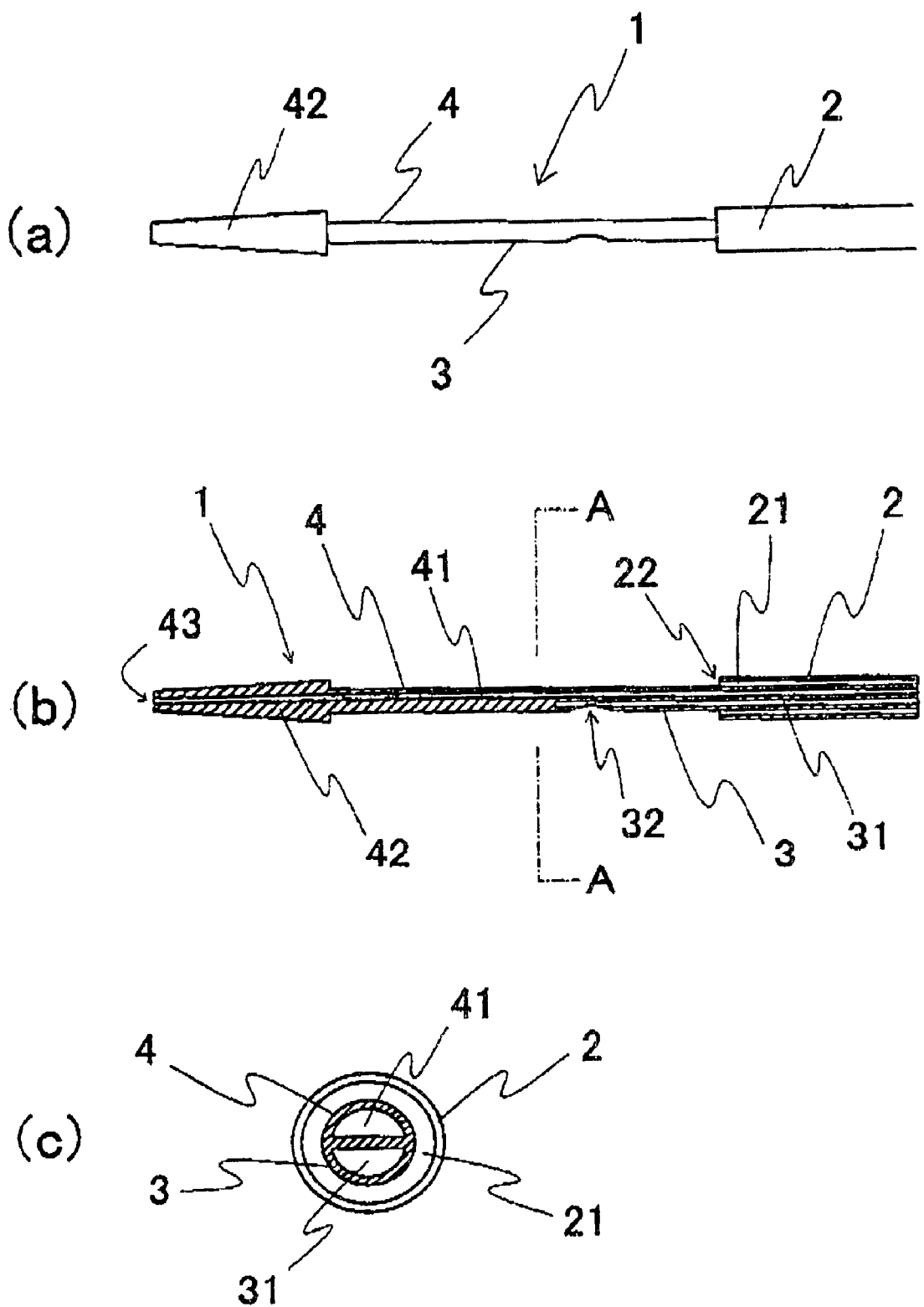
FIGS. 7(a), (b) and (c) are views illustrating, on an enlarged scale, the front end of the multi lumen catheter (A) of the invention according to a fourth embodiment.
Figure 8:
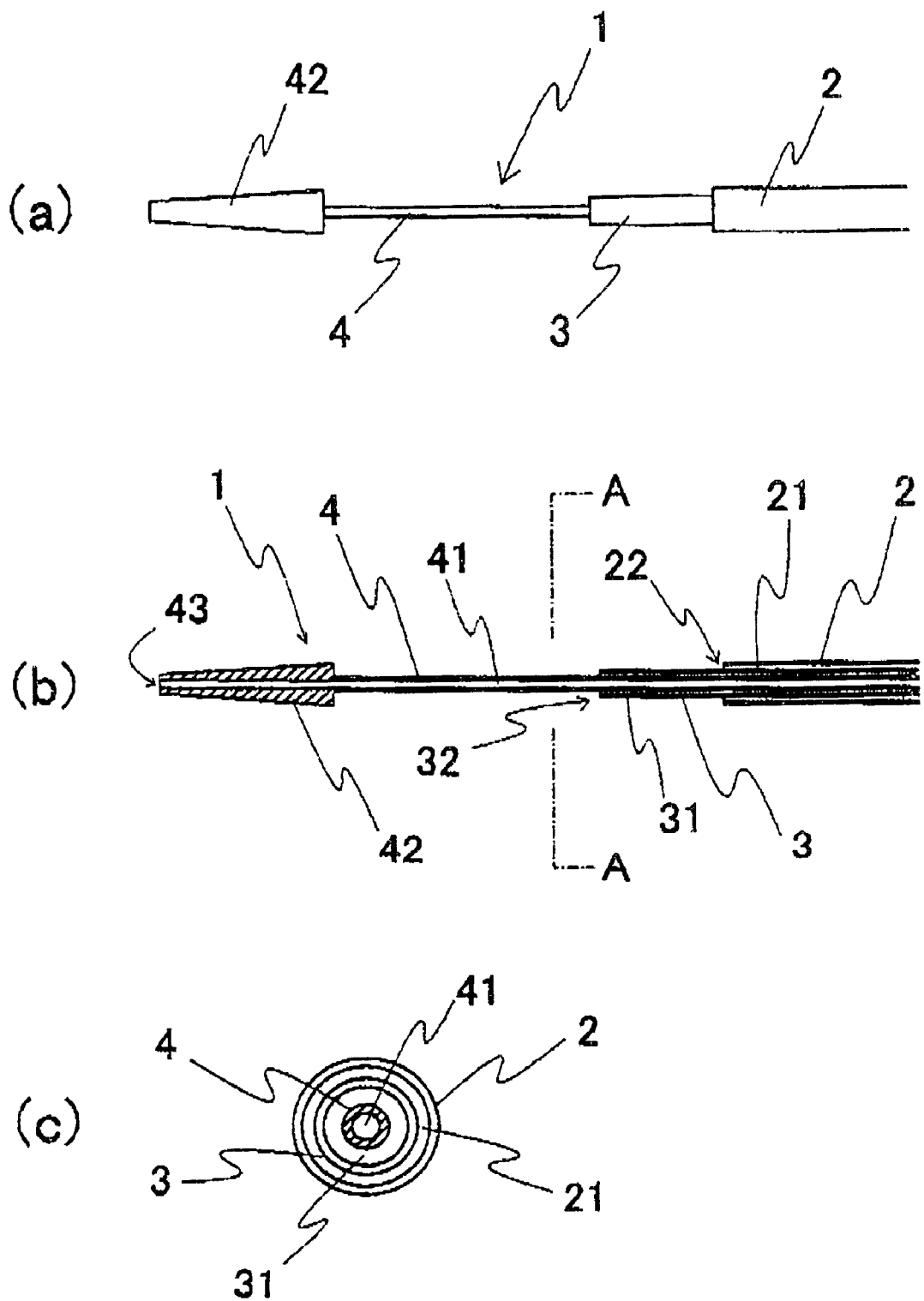
FIGS. 8(a), (b) and (c) are views illustrating, on an enlarged scale, the front end of the multi lumen catheter (A) of the invention according to a fifth embodiment.
Figure 9:
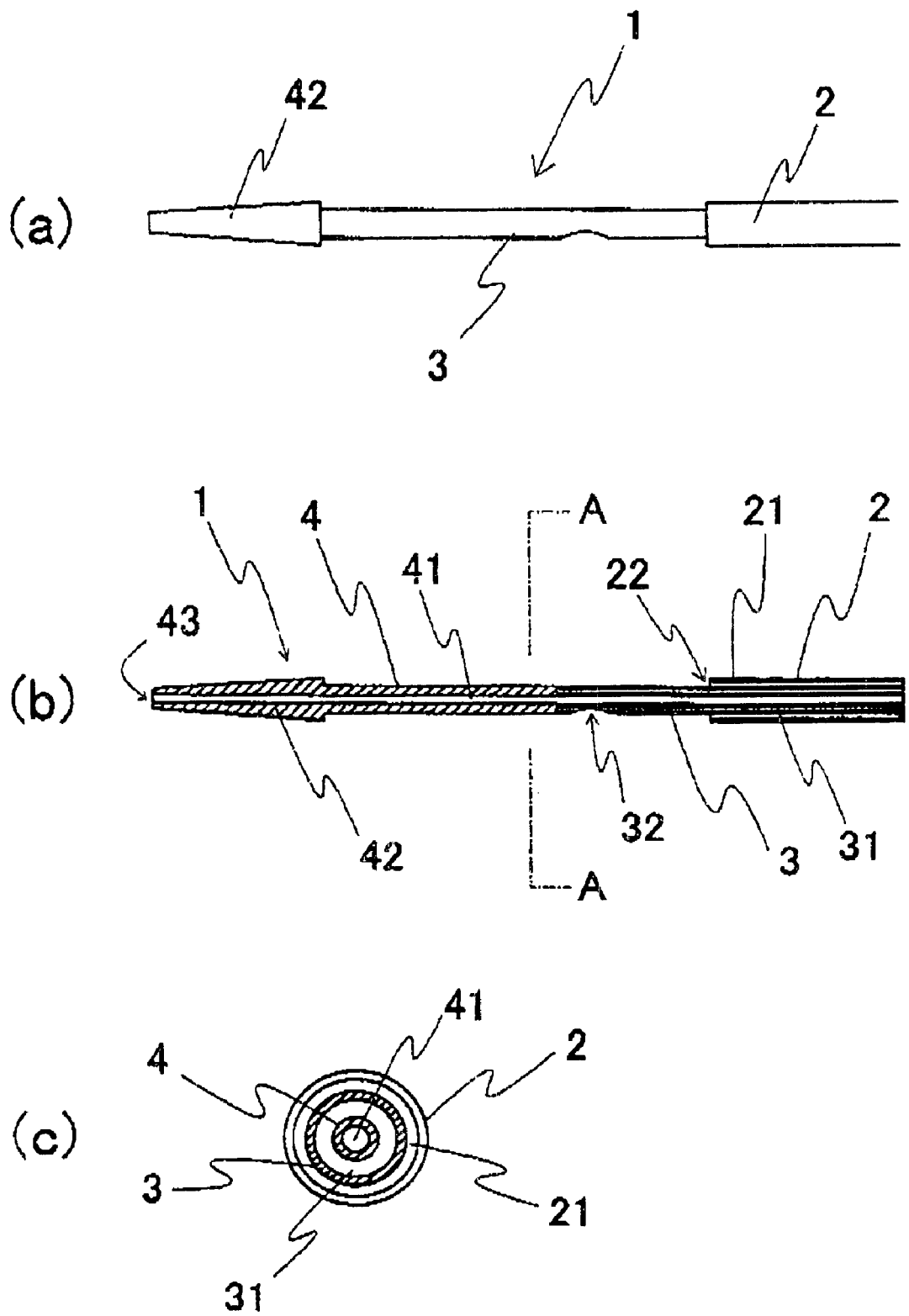
FIGS. 9(a), (b) and (c) are views illustrating, on an enlarged scale, the front end of the multi lumen catheter (A) of the invention according to a sixth embodiment.

FIG. 1 is a side view of a first embodiment of a multi-lumen catheter of the invention in a state where dialysis is being conducted, and FIG. 2 is a side view of the multi-lumen catheter of FIG. 1 in a state where dialysis is not being conducted. FIGS. 3(a), (b) and (c) are views illustrating, on an enlarged scale, the front end of the multi-lumen catheter of FIG. 1, and FIG. 4 is a view illustrating, on an enlarged scale, the front end of the multi-lumen catheter of FIG. 2. FIGS. 5(a), (b) and (c) are views illustrating, on an enlarged scale, the front end of the multi-lumen catheter of the invention according to a second embodiment, FIGS. 6(a), (b) and (c) are views illustrating, on an enlarged scale, the front end of the multi-lumen catheter of the invention according to a third embodiment, FIGS. 7(a), (b) and (c) are views illustrating, on an enlarged scale, the front end of the multi-lumen catheter of the invention according to a fourth embodiment, FIGS. 8(a), (b) and (c) are views illustrating, on an enlarged scale, the front end of the multi-lumen catheter of the invention according to a fifth embodiment, and FIGS. 9(a), (b) and (c) are views illustrating, on an enlarged scale, the front end of the multi-lumen catheter of the invention according to a sixth embodiment. In FIG. 3 and FIGS. 5 to 9, the drawings (a) are side views of the front ends, the drawings (b) are vertical sectional views of the front ends, and the drawings (c) are cross sectional views along the lines A-A in the drawings (b).

An embodiment of the multi-lumen catheter (A) of the invention will now be chiefly described with reference to FIGS. 1 to 3.

As shown in FIG. 1, the multi-lumen catheter 1 comprises an outer tube 2 having an inner cavity constituting a blood extraction lumen and a blood extraction port at an end; an inner tube 3 having an inner cavity constituting a blood return lumen and a blood return port; and a tube 4 for inserting a guide wire and having an inner cavity constituting a lumen for inserting a guide wire, and a front tip 42. As used herein, the front end stands for a side (left side in the drawing) that is inserted in the body of a patient, and the base end stands for a side (right side in the drawing) on which the connectors and the like are provided outside the body of the patient.

FIG. 3(a) is a side view illustrating, on an enlarged scale, a front end of the multi-lumen catheter 1 of FIG. 1, FIG. 3(b) being a vertical sectional view across the line A-A of the multi-lumen catheter 1 of FIG. 1 on an enlarged scale, and FIG. 3(c) being a cross sectional view along the line A-A of FIG. 3(b).

Referring to FIGS. 3(a)-(c), the outer tube 2 has a nearly circular shape in cross section, and its inner cavity constitutes a blood extraction lumen 21. At the front end of the outer tube 2, the blood extraction lumen 21 is fluid-communicated with the exterior of the catheter 1 through a blood extraction port 22 which is open toward the front end side in the axial direction of the outer tube 2. The base end of the outer tube 2 is connected to a connection portion 23 and constitutes the catheter 1 in combination with the inner tube 3 and the tube 4 for inserting the guide wire.

The blood extraction port 22 may have a shape that is obtained by simply cutting the outer tube 2 in a direction perpendicular to the axis thereof, or may have any shape such as the one obtained by cutting the outer tube 2 aslant relative to the axis thereof, or various other shapes that match the shape of the front tip so that the outer tube 2 can be liquid-tightly joined to the front tip of the tube 4 for inserting the guide wire as will be described later.

It is desired that the outer tube 2 be formed of a resin having flexibility and tensile strength, such as a polyurethane, polyethylene, polypropylene, polyamide, polyester, fluorine-containing resin or silicone resin. Further, the outer tube 2 is desirably formed by extrusion molding.

The overall length of the outer tube 2 is long enough to indwell from the skin of a patient to a blood vessel, and is selected to be, for example, from 100 to 300 mm. The size of the outer tube 2 is suitably selected depending upon the material constituting the outer tube 2, and is, usually, from 3 to 5 mm in outer diameter, from 2 to 4.6 mm in inner diameter, and from 0.2 to 0.5 mm in thickness. When the outer diameter of the outer tube 2 is greater than the above value, a patient suffers increased pain when the catheter is introduced into the patient's body. When the inner diameter of the outer tube 2 is smaller than the above value, the blood flows through at a decreased flow rate and causes deterioration of the efficiency of dialysis therapy. It is further desired that the thickness of the outer tube 2 be as thin as possible within a range in which it maintains a sufficiently large strength without kinking or without being torn apart when it is introduced into the patient's body and does not cause a decrease in the flow rate of blood flowing therethrough.

The connection portion 23 is a hollow tube connected to the base end of the outer tube 2 by means such as melt-adhesion. The connection portion 23 communicates with the blood extraction lumen 21, and has an inner cavity of a size which permits the inner tube 3 and the tube 4 for inserting the guide wire to be inserted therein. In order to introduce the blood flowing from the blood extraction lumen 21 to the dialyzer, the connection portion 23 is provided with a blood extraction tube 231 shown in FIG. 1 as well as with a connector 232 for connecting the blood extraction tube 231 to the dialyzer, and other known parts necessary for carrying out dialysis.

The connection portion 23 is made of the same resin as the resin constituting the outer tube 2, i.e., a flexible resin such as polyurethane or silicone resin. The connection portion 23 is formed desirably by injection molding.

The inner tube 3 is inserted in the outer tube 2 and has an inner cavity that constitutes a blood return lumen 31. The blood return lumen 31 is liquid-communicated with the exterior of the catheter 1 through a blood return port 32. A movable portion 33 is connected to the base end of the inner tube 3 so as to be also secured to the base end of the tube 4 for inserting the guide wire.

Referring again to FIGS. 3(a)-(c), when the front end of the inner tube 3 is not secured to a front tip 42 of the tube 4 for inserting the guide wire, it is desired that the blood return port 32 is open at the end of the inner tube 3 facing the front end side in the axial direction of the inner tube 3. Referring to FIGS. 5(a)-(c) which illustrate a second embodiment of catheter (A) of the invention, when the end of the inner tube 3 is secured to the front tip 42 of the tube 4 for inserting the guide wire, it is desired that the blood return port 32 be a side port opening in the side surface of the inner tube. There is no particular limitation to the shape of the blood return port 32 provided, however, that it does not hinder the blood from being discharged. Desirably, however, the port has a nearly circular shape.

The blood return port 32 of the inner tube 3 is formed on the front side of the blood extraction port 22 when the dialysis is being conducted. Here, it is desired that the distance between the blood return port 32 and the blood extraction port 22 be from 5 to 70 mm and, more desirably, from 20 to 30 mm. When the distance is more than 70 mm, the sliding distance for joining the outer tube 2 to the front tip 42 increases as will be described later making it difficult to carry out the operation. When the distance is less than 5 mm, on the other hand, the blood discharged from the blood return port 32 may be sucked through the blood extraction port 22, which may decrease the dialysis efficiency.

The material constituting the inner tube 3 and the method of molding the inner tube 3 are preferably the same as those used for the above outer tube 2.

The movable portion 33 is a hollow tube connected to the inner tube 3 by adhesion or insertion molding. The movable portion 33 has an inner cavity that communicates with the blood return lumen 31. The movable portion 33 is arranged on the base end side of the connection portion 23 so as to slide, and the inner diameter of the movable portion 33 on the front end side is selected to be slightly greater than the outer diameter of which on the base end side of the connection portion 23. The movable portion 33 is provided with a blood return tube 331 for guiding the dialyzed blood to the blood return lumen 31 from the dialyzer (not shown in FIG. 1), a connector 332 for connecting the blood return tube 331 to the dialyzer, and with any other known parts necessary for conducting dialysis. The material constituting the movable portion 33 and the molding method thereof are the same as those for the above connection portion 23.

The tube 4 for inserting the guide wire is inserted in the outer tube 2, and its inner cavity constitutes a lumen 41 for inserting the guide wire. A front tip 42 of a tapered shape of which the outer diameter decreases toward the front end side is formed at the front end of the tube 4 for inserting the guide wire. The front tip 42 is a hollow member and its inner cavity communicates with the lumen for inserting the guide wire. Further, the inner cavity of the front tip 42 communicates with the exterior of the catheter 1 through an opening 43 which is open at the front end of the front tip 42 toward the front end side in the axial direction of the inner tube 4 for inserting the guide wire. The movable portion 33 connected to the base end of the inner tube 3 is also connected to the base end of the lumen 41 for inserting the guide wire.

The material constituting the tube 4 for inserting the guide wire and the molding method thereof are preferably the same as those used for the above outer tube 2.

The tube 4 for inserting the guide wire is connected at its base end to the movable portion 33. Therefore, the movable portion 33 has an inner cavity that communicates with the lumen 41 for inserting the guide wire separately from the inner cavity which communicates with the blood return lumen 31. As shown in FIG. 1, further, the movable portion 33 is provided with a tube 333 for inserting the guide wire to introduce the guide wire into the lumen 41 for inserting the guide wire, and with a connector 334.

The inner tube 3 and the tube 4 for inserting the guide wire are independent tubes, and their lumens are completely separate from each other from the front end side thereof up to the tubes 331 and 333 on the base end side through the moving portion 33.

As shown in FIGS. 3(a)-(c) and 5(a)-(c), the inner tube 3 and the tube 4 for inserting the guide wire may both have a nearly circular shape in cross section. When the inner tube 3 is connected to the tube 4 for inserting the guide wire at the base end portion, i.e., at the movable portion 33 only as shown in FIGS. 3(a) and (b), the overall length of the inner tube 3 is selected to be smaller than the overall length of the tube 4 for inserting the guide wire, and the blood return port 32 of the inner tube 3 is so formed as to be open toward the front end side in the axial direction. Referring, further, to FIGS. 5(a) and (b), when the inner tube 3 is connected to the tube 4 for inserting the guide wire at the movable portion 33 on the base end side and is also connected to the tube 4 at the front tip 42, the blood return port 32 of the inner tube 3 is a side port formed in the side surface of the inner tube 3.

Further examples of the shapes of the inner tube 3 and the tube 4 for inserting the guide wire are shown in FIGS. 6(a)-(c) and 7(a)-(c) which illustrate the multi-lumen catheter (A) of the invention according to a third embodiment and a fourth embodiment, in which the inner tube 3 shares a portion of the wall over the full length thereof. In this case, a desired shape is that the inner cavity of a tube is partitioned by a piece of wall. This shape may be formed by connecting two tubes of a semi-circular shape in cross section, or may be an integrally molded one.

When the inner tube 3 is connected to the tube 4 for inserting the guide wire at the movable portion 33 only as shown in FIGS. 6(a) and (b), the overall length of the inner tube 3 is selected to be smaller than the overall length of the tube 4 for inserting the guide wire, and the blood return port 32 of the inner tube 3 is so formed as to be open toward the front end side in the axial direction. Referring, further, to FIGS. 7(a) and (b), when the inner tube 3 is connected to the tube 4 for inserting the guide wire at the movable portion 33 on the base end side and is also connected to the tube 4 at the front tip 42, it is desired that the blood return port 32 of the inner tube 3 be a side port formed in the side surface of the inner tube 3.

Further examples of the shapes of the inner tube 3 and the tube 4 for inserting the guide wire are shown in FIGS. 8(a)-(c) and 9(a)-(c) which illustrate the multi-lumen catheter of the first aspect of the invention according to a fifth embodiment and a sixth embodiment, in which the tube 4 for inserting the guide wire is inserted in the inner tube 3.

Referring to FIGS. 5(a) and (b), 7(a) and (b) and 9(a) and (b), when the front end of the inner tube 3 is connected to the front tip 42, the blood return port 32 is a side port. Therefore, the front end side of the blood return port 32 of the blood return lumen 31 becomes a blood reservoir where thrombi may be formed. It is therefore desired that the inner tube 3 has a construction in which the front end side of the blood return port 32 of the blood return lumen 31 is closed up to the front tip 42, or has a construction in which, though not illustrated, a means for closing the blood return lumen 31 is inserted on the front end side of the blood return port 32.

When dialysis is being conducted as shown in FIGS. 1, 3 and 5 to 9, the outer tube 2, inner tube 3 and tube 4 for inserting the guide wire are such that the front tip 42, blood return port 32 and blood extraction port 22 are arranged in this order from the front end side. In this state, the blood extraction lumen 21 communicates with the exterior of the catheter 1 through the blood extraction port 22, and the blood return lumen 31 communicates with the exterior of the catheter 1 through the blood return port 32.

When dialysis is not being carried out, on the other hand, heparin is introduced into the blood extraction lumen 21 and the blood return lumen 31. At this moment as shown in FIGS. 2 and 4, the moving portion 33 is slid toward the base end side relative to the connection portion 23, and the front end of the outer tube 2 is liquid-tightly joined to the base end of the front tip 42, whereby communication with the exterior of the catheter 1 is shut off at the blood extraction port 31 and at the blood return port 32. Even when the catheter 1 indwells in the body for extended periods of time, therefore, no blood enters into the blood extraction lumen 21 from the blood extraction port 22, or into the blood return lumen 31 from the blood return port 32, no thrombi are formed, and heparin locking is reliably maintained.

As the moving portion 33 slides relative to the connection portion 23, the inner tube 3 and the tube 4 for inserting the guide wire connected to the moving portion 33 also slide relative to the outer tube 2 connected to the connection portion 23. As the inner tube 3 and the tube 4 for inserting the guide wire slide relative to the outer tube 2, the front tip 42 is correctly guided to the front end of the outer tube 2 and is liquid-tightly joined thereto.

Figure 10:
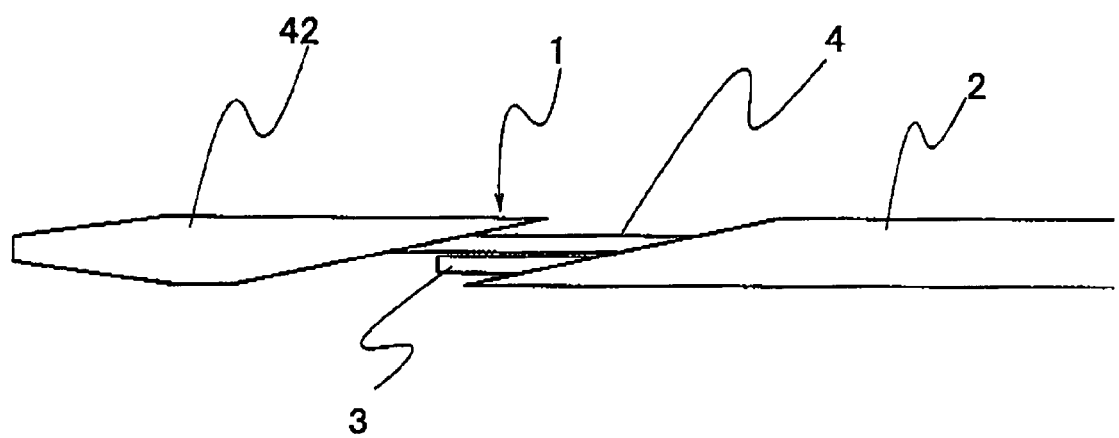
FIG. 10 is a view illustrating, on an enlarged scale, the front end of the multi lumen catheter (A) according to a further embodiment of the invention.

There is no particular limitation on the shapes of the base end of the front tip 42 and on the front end of the outer tube 2, provided that the communication between the interior and the exterior of the catheter 1 is shut off in the blood extraction port 22 and in the blood return port 32 by the junction thereof. For example, the junction surface between the front tip 42 and the outer tube 2 may be formed on a plane at right angles with the long axis of the multi-lumen catheter 1 as shown in FIGS. 1 to 9 or may be formed on a plane intersecting the long axis of the multi-lumen catheter 1 at an obtuse angle as shown in FIG. 10. When the multi-lumen catheter 1 has the junction surface as shown in FIG. 10, the sliding distance of the moving portion 33 can be minimized to shut off the communication in the blood extraction port 22 and in the blood return port 32, and the operation becomes easier.

The multi-lumen catheter (A) of the invention may be provided with a locking mechanism for securing the connection portion 23 and the movable portion 33 at a position for maintaining the outer tube 1, the inner tube 2 and the tube 4 for inserting the guide wire in the arrangement thereof when dialysis is being carried out exterior of the catheter 1 is not shut off. The locking mechanism is preferably one based on the engagement of a protuberance formed on the outer surface of the connection portion 23 with a groove which is formed in the moving portion 33 and extends in the axial direction thereof.

Further, the multi-lumen catheter 1 may be provided with a locking mechanism for securing the connection portion 23 and the moving portion 33 at positions of maintaining the state where the front tip 42 of the tube 4 for inserting the guide wire is joined to the outer tube 2 when the dialysis is not being carried out, i.e., in a state where communication between the interior and exterior of the catheter 1 is shut off. The locking mechanism may be the same as the locking mechanism for maintaining the arrangement of the tubes when dialysis is being carried out.

It is desired that the catheter 1 be provided with both the locking mechanism for maintaining the arrangement of the tubes when dialysis is being carried out and with the locking mechanism for maintaining the arrangement of the tubes when dialysis is not being carried out. The locking mechanisms in this case are based upon the engagement of the protuberance formed on the outer surface of the connection portion 23 with the groove formed in the moving portion 33 and which extends in the axial direction, the groove having a U-shape with its ends bending in a direction perpendicular to the axis, or having a dumbbell shape with wide areas at both ends and with a narrow area at an intermediate portion.

In the multi-lumen catheter (A) of the invention, even if blood remains in the blood extraction lumen 21 or the blood return lumen 31 after heparin has been introduced, the blood extraction lumen 21 liquid-communicates with the blood return lumen 31 through the blood extraction port 22 and the blood return port 32 even in a state where the outer tube 2 and the front tip 42 are joined together and the communication between the interior and the exterior of the catheter 1 is shut off at the blood extraction port 22 and at the blood return port 32. Therefore, a liquid such as heparin can be introduced through one lumen and discharged through the other lumen thereby to effectively wash away the blood remaining in the lumens. This constitution makes it possible for the catheter 1 to be indwelt safely and to stay in the body of a patient for further extended periods of time.

Next, described below with reference to FIGS. 1 to 4 is how to use the multi-lumen catheter (A) of the invention.

First, the multi-lumen catheter 1 of the invention is introduced into the body of a patient in a state where the front tip 42 of the tube 4 for inserting the guide wire is joined to the outer tube 2 as illustrated in FIG. 2. To introduce the catheter 1, the base end of a guide wire that has been introduced in the patient in advance by known means is inserted through the opening 43 of the front tip 42 so that the front end of the guide wire remains in a blood vessel and the base end stays outside the body, and the catheter 1 is inserted in the blood vessel along the guide wire. Due to this operation, the base end of the guide wire enters the movable portion 33 passing through the lumen 41 for inserting the guide wire, and protrudes from the connector 334 through the tube 333 for inserting the guide wire. When the catheter 1 is inserted up to a predetermined position, the guide wire in the catheter 1 is pulled out through the connector 334, and the catheter 1 is secured to the body of the patient by using tape or the like. If wings 5 are provided on the surface of the catheter 1, the catheter 1 can be maintained reliably secured for extended periods of time, which is desirable. Tube 333 is temporarily closed by an appropriate means. Heparin may be introduced into tube 333 before it is closed.

Prior to starting the dialysis, the catheter 1 inserted in the blood vessel of the patient is connected to the dialyzer through the connector 232 of the blood extraction tube 231 and the connector 332 of the blood return tube 331. Then, the moving portion 33 is slid toward the front end side relative to the connection portion 23 as shown in FIG. 1. As shown in FIG. 3, the junction is broken between the front tip 42 and the outer tube 2, whereby the blood extraction lumen 21 communicates with the exterior of the catheter 1 through the blood extraction port 22, and the blood return lumen 31 is communicated with the exterior of the catheter 1 through the blood return port 32.

After the start of dialysis, the blood enters the blood extraction lumen 21 through the blood extraction port 22 and is sent to the dialyzer through the blood extraction tube 231. The blood treated through the dialyzer enters the blood return lumen 31 through the blood return tube 331, and is returned back into the blood vessel through the blood return port 32.

After the dialysis has been finished, the connectors 232 and 332 are disconnected from the dialyzer, and the blood extraction lumen 21 and the blood return lumen 31 are filled with heparin. Next, the moving portion 33 is slid toward the base end side relative to the connection portion 23 to a closed position as shown in FIG. 1. As shown in FIG. 4, the front tip 42 and the outer tube 2 are liquid-tightly joined together, and the communication with the exterior of the catheter 1 is shut off at the blood extraction port 22 in the blood extraction lumen 21 and at the blood return port 32 in the blood return lumen 31.

In this case, when the blood remains in the blood extraction lumen 21 and in the blood return lumen 31, a liquid such as heparin may, as required, be introduced through one lumen and discharged through the other lumen to wash away the blood remaining in these lumens. Thereafter, the blood extraction tube 231 and the blood return tube 331 are closed by any suitable means, and the catheter 1 is left to stay in the blood vessel until the dialysis is conducted next time.

The dialysis is conducted repetitively, and the moving portion 33 is slid toward the front end side or the base end side relative to the connection portion 23 each time. Parts such as tubes connected to the moving portion 33 and to the connection portion 23 communicate with the blood extraction lumen 21, blood return lumen 31 and lumen 41 for inserting the guide wire. As required, however, means are suitably provided to shut off the communication to prevent the infiltration of bacteria and the leakage of liquid while the catheter is left to stay in the blood vessel.

In the multi-lumen catheter (A) of the invention, a means for closing the blood extraction port and the blood return port, which so far has been a sheath provided on the outer side of a conventional catheter, is an outer tube that constitutes the blood extraction lumen. Therefore, the wall portion is not increased in cross section, the diameter of the catheter is not increased and does not give an increased burden to a patient, and the flow rate of the blood is not decreased. Unlike the conventional catheters, further, no gap exists between the catheter and the sheath, and there is no need to design a structure for maintaining liquid tightness in the gap.

In the multi-lumen catheter of the invention, further, the front tip is joined to the outer tube when dialysis is not being conducted, and the blood extraction lumen and the blood return lumen are shut off from the exterior of the catheter. Accordingly, the blood extraction port and the blood return port are not exposed to the blood and no blood enters into the lumens to form thrombi. Even in a state of being shut off from the exterior, the blood extraction lumen and the blood return lumen communicate with each other inside the catheter through the blood extraction port and the blood return port. Even in case the blood remains in the lumens, therefore, a liquid such as heparin is introduced from one lumen and is discharged from the other lumen to efficiently wash the two lumens. Accordingly, blood does not remain in the catheter and heparin locking is reliably maintained and it is possible to safely leave the catheter in the blood vessel of a patient for extended periods of time.

Catheter (B)

Another embodiment of the present invention is a multi-lumen catheter (B) comprising an outer tube 2 having an inner cavity constituting a blood extraction lumen 21 and a blood return lumen 31, a blood extraction port 22 which is open toward the front end side in the axial direction and provides communicate between said blood extraction lumen 21 with the exterior of the catheter, and a blood return port 22 open toward the front end side in the axial direction on the front side of said blood extraction port 22 and provides communicate between said blood return lumen 31 with the exterior of the catheter 1; and an inner tube 4 having an inner cavity constituting a lumen 41 for inserting a guide wire and having a front tip 42 of a tapered shape;

wherein said inner tube 4 is inserted in said outer tube 2, and is allowed to slide relative to said outer tube 2 and when said outer tube 2 and said inner tube 4 are in such an order that the front tip 42, the blood return port 32 and the blood extraction port 22 are successively arranged in order from the front end side, the blood extraction lumen 21 with the blood extraction port 22 and the blood return lumen 31 with the blood return port 32 communicate with the exterior of the catheter 1, and when the front tip 42 of said inner tube 3 is joined to the front end of said outer tube 2, the communication of said blood extraction lumen 21 and said blood return lumen 31 from the exterior of the catheter 1 is shut off.

Mode of Operation

The multi-lumen catheter (B) of the present invention has a structure in which the outer tube constitutes a blood extraction lumen and a blood return lumen in the inside while performing the function of a sheath, and the inner tube constituting the lumen for inserting a guide wire is inserted in the outer tube. This constitution makes it possible to provide a catheter having the advantages of a catheter equipped with a sheath without increasing the ratio of the wall portion of the catheter with the conventional catheters. Therefore, the multi-lumen catheter of the invention possesses the above constitution with a diameter comparable to that of the conventional catheters, without giving an increased burden to the patient and without decreasing the flow rate through the blood extraction lumen and the blood return lumen.

In the multi-lumen catheter (B) of the invention, further, as with the multi-lumen catheter (A) of the invention, the blood extraction port and the blood return port are closed as the front tip of the tube for inserting the guide wire is joined to the outer tube and, hence, no gap exists between the catheter and the sheath. This eliminates the need of designing a structure for maintaining liquid tightness in the gap between the sheath and the catheter unlike the conventional catheter.

Multi-lumen catheter (B) of the invention will now be described in detail with reference to preferred embodiments shown in FIGS. 11 to 18 of the accompanying drawings. However, the invention is in no way limited these embodiments.

Figure 11:
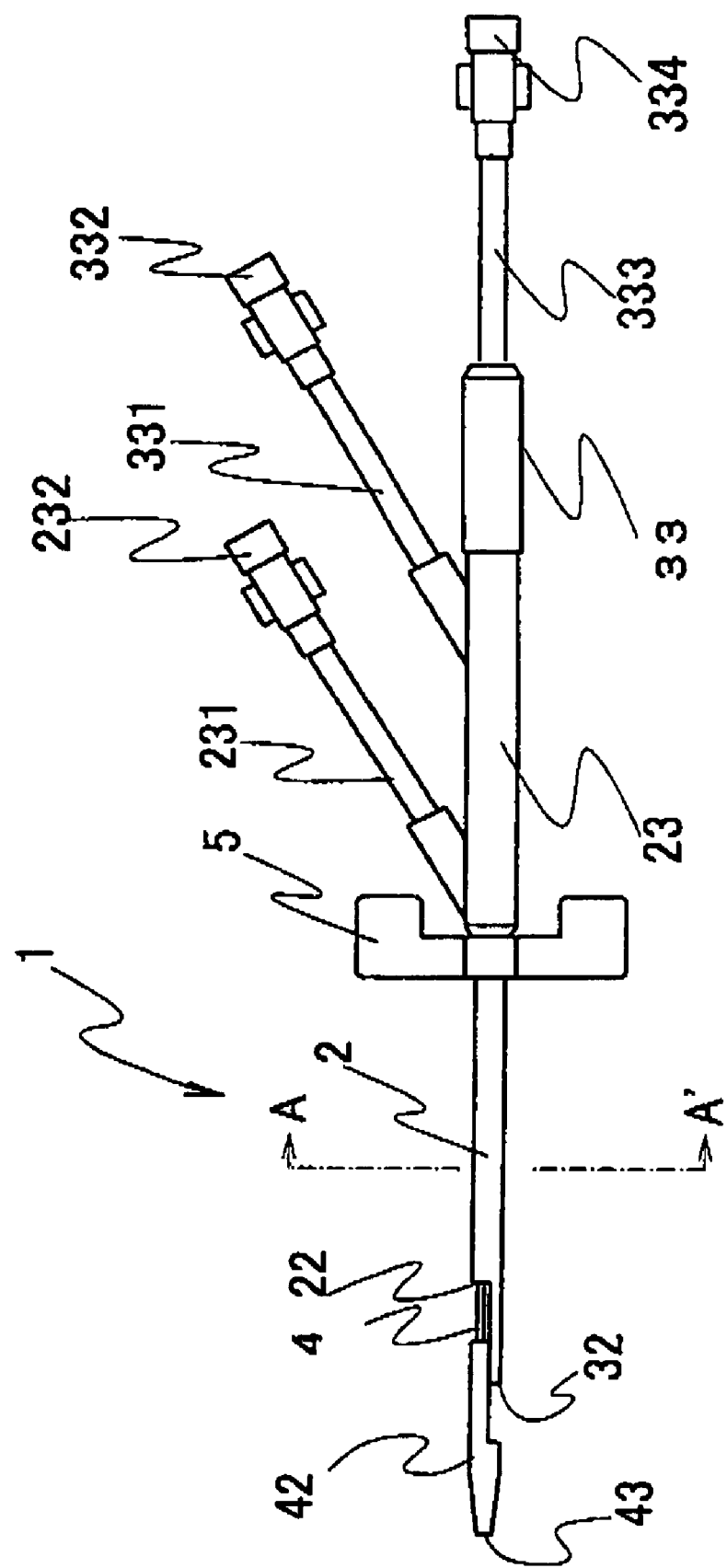
FIG. 11 is a side view of an embodiment of a multi lumen catheter (B) of the invention in a state where the communication has not been shut off in the blood extraction port and in the blood return port.
Figure 12:
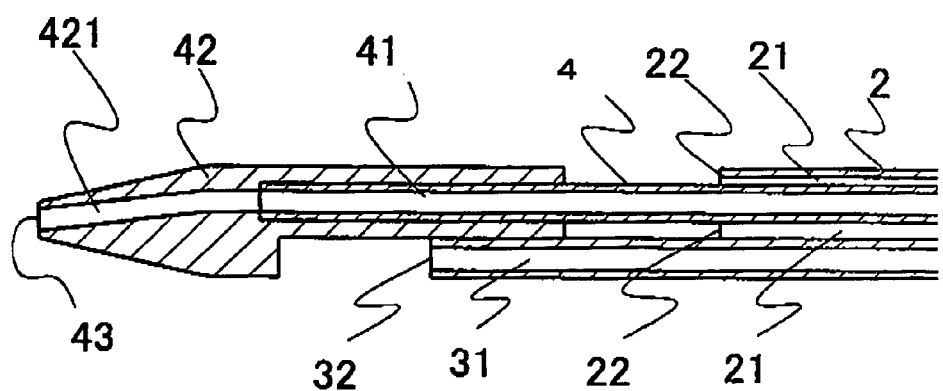
FIG. 12 is a sectional view showing, on an enlarged scale, a front end of the multi lumen catheter of FIG. 11.
Figure 14:
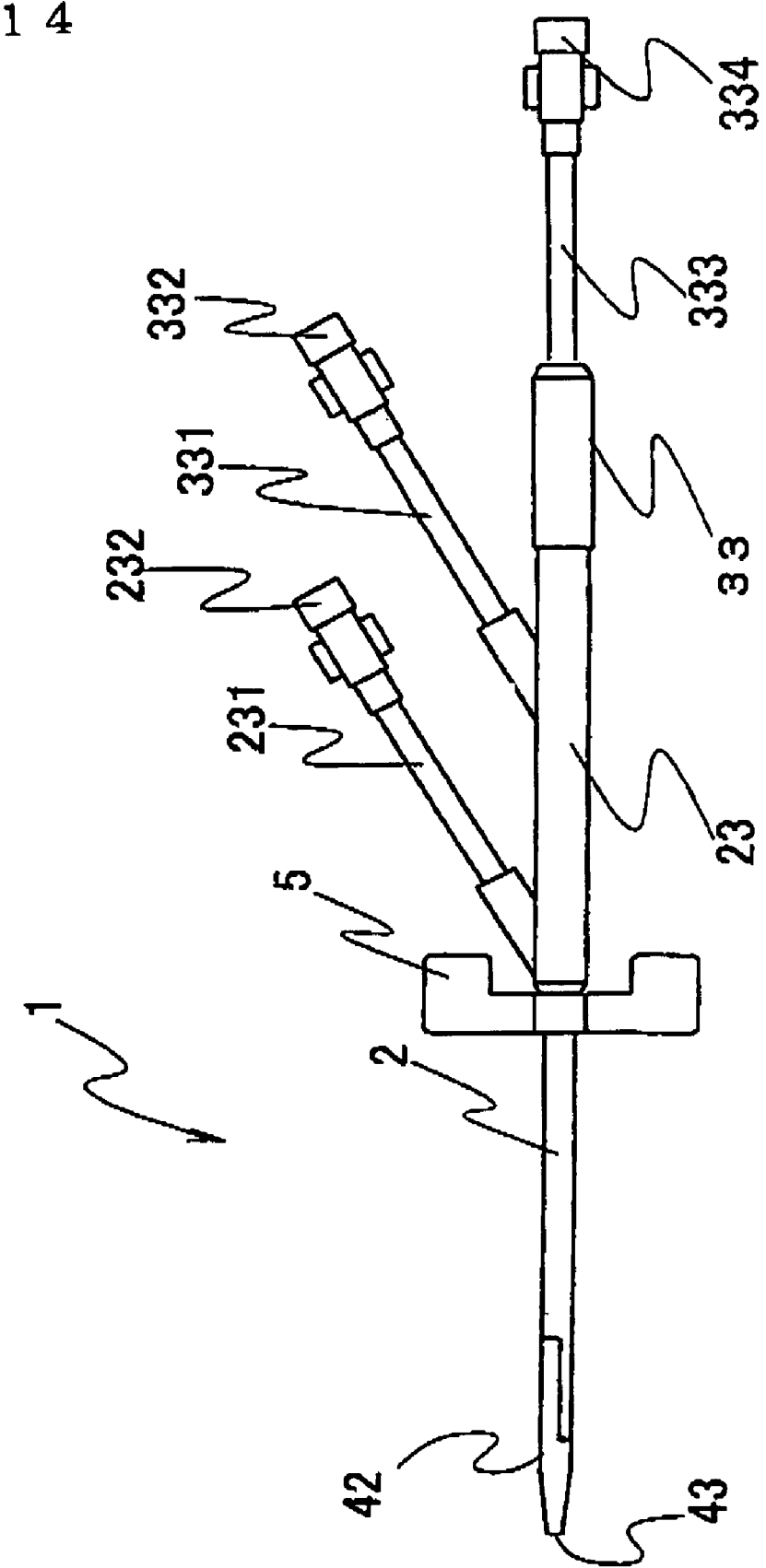
FIG. 14 is a side view of the multi lumen catheter of FIG. 11 in a state where the communication has been shut off in the blood extraction port and in the blood return port.
Figure 15:
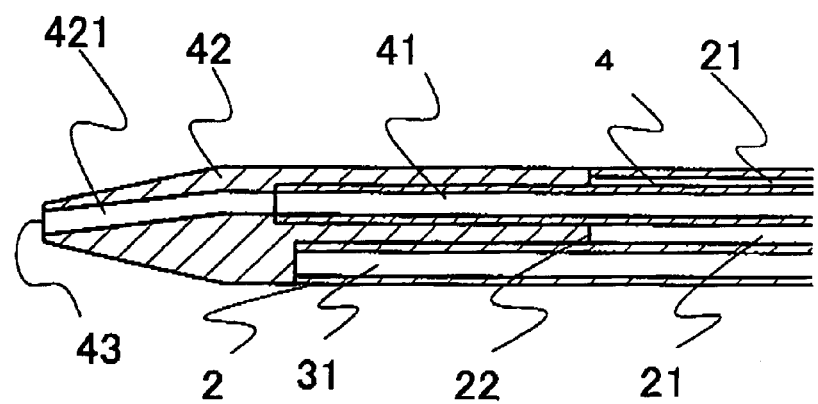
FIG. 15 is a sectional view showing, on an enlarged scale, a front end of the multi lumen catheter of FIG. 14.
Figure 16:
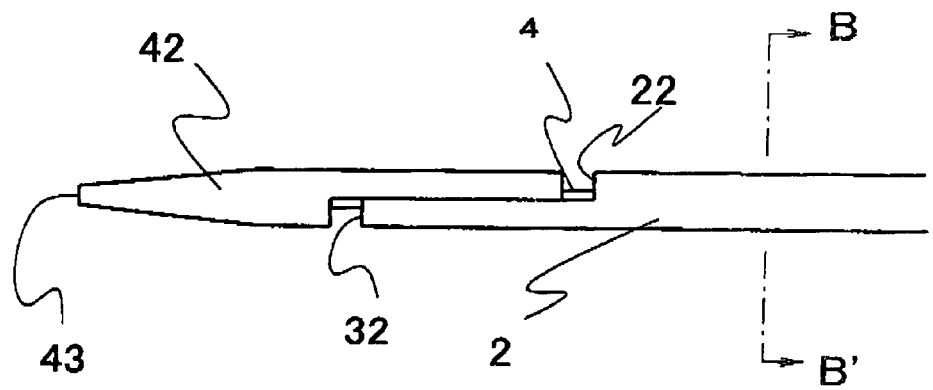
FIG. 16 is a view illustrating, on an enlarged scale, the front end of another embodiment of the multi lumen catheter (B) of the invention in a state where the communication has not been shut off in the blood extraction port and in the blood return port.
Figure 18:
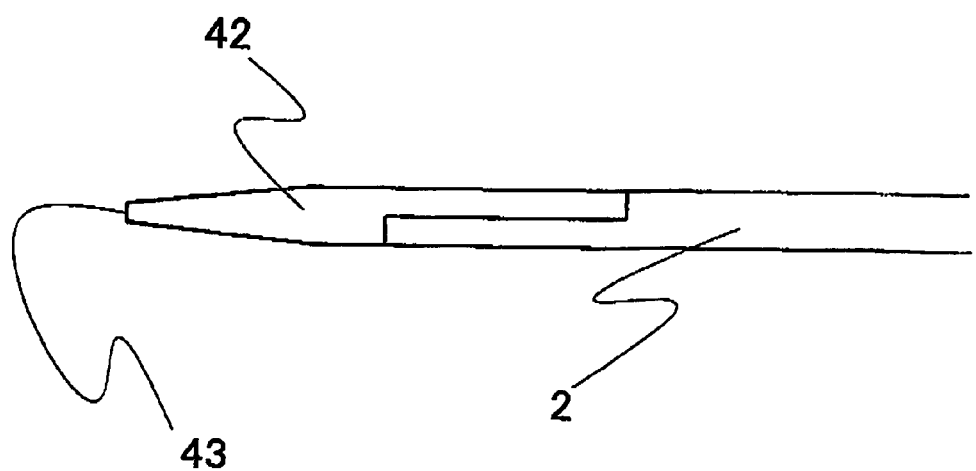
FIG. 18 is a view illustrating, on an enlarged scale, the front end of the multi lumen catheter of FIG. 16 in a state where the communication has been shut off in the blood extraction port and in the blood return port.

FIGS. 11 and 12 are views illustrating a first embodiment of multi-lumen catheter (B) of the invention in a state where the communication has not been shut off with the blood extraction port and the blood return port, and FIGS. 14 and 15 are views illustrating the multi-lumen catheter of FIG. 11 in a state where the communication is shut-off with the blood extraction port and the blood return port. FIGS. 16 and 18 are views illustrating a second embodiment of multi-lumen catheter (B) of the invention.

The first embodiment of multi-lumen catheter (B) of the invention will now be chiefly described with reference to FIGS. 11 to 15.

As illustrated in the side views of the multi-lumen catheter (B) of the invention of FIGS. 11 and 14, the multi-lumen catheter 1 comprises an outer tube 2 having an inner cavity constituting a blood extraction lumen and a blood return lumen, a blood extraction port 22 and a blood return port 32; and an inner tube 4 having an inner cavity constituting a lumen for inserting a guide wire and a front tip 42. As with the description of catheter (A), the front end means a side (left side in the drawing) that is inserted in the body of a patient, and the base end means a side (right side in the drawing) where the connectors and the like are provided outside the body of the patient.

Figure 13:
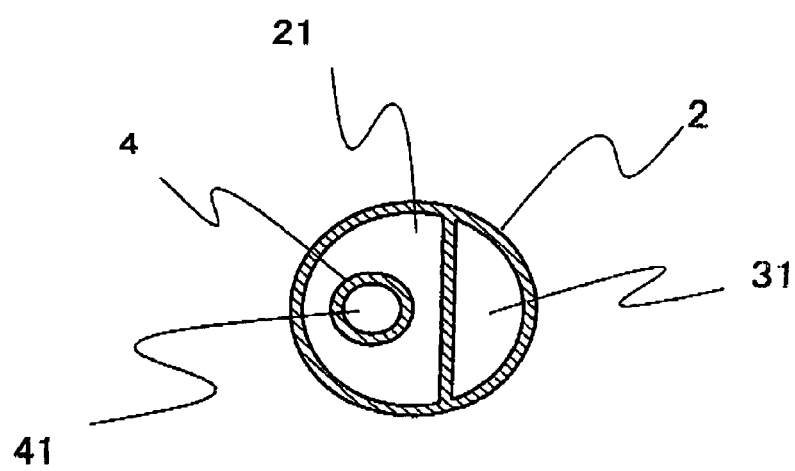
FIG. 13 is a sectional view along the line A-A of the multi lumen catheter of FIG. 11 on an enlarged scale.

FIG. 12 is a sectional view illustrating, on an enlarged scale, a front end of the multi-lumen catheter 1 of FIG. 11, and FIG. 13 is a sectional view across the line A-A of the multi-lumen catheter 1 of FIG. 11 on an enlarged scale. FIG. 15 is a sectional view illustrating the front end of the multi-lumen catheter 1 of FIG. 14 on an enlarged scale.

Referring to FIGS. 12 and 13, the outer tube 2 in the multi-lumen catheter 1 of the invention has, preferably, a nearly circular shape in cross section, and the inner cavity thereof constitutes a blood extraction lumen 21 and a blood return lumen 31. At the front end of the outer tube 2, the blood extraction lumen 21 fluid-communicates with the exterior of the catheter 1 through the blood extraction port 22 which is open toward the front end side in the axial direction of the outer tube 2. The blood return lumen 31, too, fluid-communicates with the exterior of the catheter 1 at the front end of the outer tube 2 through the blood return port 32 which is open toward the front end side in the axial direction of the outer tube 2.

It is desired that the blood return port 32 is formed on the front side of the blood extraction port 22. Here, it is desired that the distance between the blood return port 32 and the blood extraction port 22 is from 5 to 70 mm and, more desirably, from 20 to 30 mm. When the distance is not shorter than 70 mm, the sliding distance increases for joining the outer tube 2 to the front tip 42 as will be described later making it difficult to carry out the operation. When the distance is not longer than 5 mm, on the other hand, the blood discharged from the blood return port 32 may be sucked through the blood extraction port 22, which may lower the dialysis efficiency.

It is desired that the outer tube 2 is formed of a resin having flexibility and tensile strength, such as polyurethane, polyethylene, polypropylene, polyamide, polyester, fluorine-containing resin or silicone resin. Further, the outer tube 2 is desirably formed by extrusion molding.

The overall length is long enough to indwell from the skin of a patient to a blood vessel, and is selected to be, for example, from 100 to 300 mm. The size of the outer tube 2 is suitably selected depending upon the material constituting the outer tube 2, and is, usually, from 3 to 5 mm in outer diameter, from 2 to 4.6 mm in inner diameter, and from 0.2 to 0.5 mm in thickness. When the outer diameter of the outer tube 2 is greater than the above value, the patient suffers increased pain when the catheter is introduced into the patient's body. When the inner diameter of the outer tube 2 is smaller than the above value, the blood flows through at a decreased flow rate and causes deterioration of the efficiency of dialysis therapy. It is further desired that the thickness of the outer tube 2 be as small as possible within a range in which it maintains a sufficiently large strength without kinking or without being torn apart when it is introduced into the patient's body and without causing a decrease in the flow rate of blood flowing therethrough.

The outer tube 2 has a connection portion 23 connected to a base end thereof as shown in FIG. 11 thereby to constitute the catheter 1 with the inner tube 4 that is described later being inserted therein so as to slide. The connection portion 23 is a hollow pipe connected to the base end of the outer tube 2 by means such as heated melt-adhesion. The connection portion 23 communicates with the blood extraction lumen 21 and the blood return lumen 31, and has an inner cavity of a size which permits the inner tube 4 to be inserted therein. In order to introduce the blood from the blood extraction lumen 21 to the dialyzer and to return the blood back again to the patient through the blood return lumen 31, the connection portion 23 is provided with a blood extraction tube 231 and a blood return tube 331 as shown in FIG. 11 as well as with connectors 232, 332 for connecting tubes 231 and 331 to the dialyzer, and other known parts necessary for carrying out the dialysis.

The connection portion 23 is made of the same resin as the resin constituting the outer tube 2, such as a flexible resin such as polyurethane or silicone resin. The connection portion 23 is formed desirably by injection molding.

The inner tube 4 is inserted in the outer tube 2, and its inner cavity constitutes a lumen 41 for inserting a guide wire. A front tip 42 of a tapered shape is formed at the front end of the inner tube 4, the front tip 42 having an outer diameter decreasing toward the front end side. The front tip 42 has a passage 421 formed therein so as to communicate with the lumen 42 for inserting the guide wire. Further, a front end of the passage 421 in the front tip 42 communicates with the exterior of the catheter 1 through an opening 43 which is open at the front end of the front tip 42 toward the front end side in the axial direction of the inner tube 4. Further, the base end of the inner tube 4 is inserted in the connection portion 23, and a movable portion shown in FIG. 11 is connected to the base end thereof. The material constituting the inner tube 4 and the molding method thereof are preferably the same as those used for the above outer tube 2.

The movable portion 33 is a hollow tube connected to the base end of the inner tube 4 by adhesion or insertion molding. The movable portion 33 has an inner cavity capable of communicating with the lumen 41 for inserting the guide wire. The movable portion 33 is arranged on the base end side of the connection portion 23 so as to slide, and has an inner diameter on the front end side which is slightly greater than the outer diameter of the connection portion 23 on the base end side thereof. The movable portion 33 is provided with a tube 333 for inserting the guide wire and a connector 334 for introducing the guide wire into the lumen 41 for inserting the guide wire.

Figure 17:
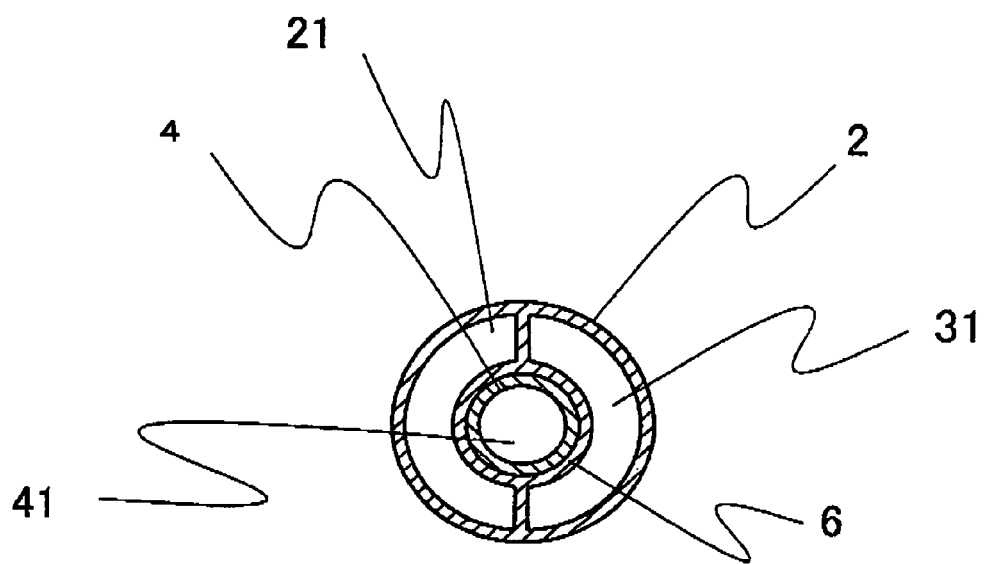
FIG. 17 is a sectional view along the line B-B of the multi lumen catheter of FIG. 16 on an enlarged scale.

FIG. 16 is a side view illustrating, on an enlarged scale, an embodiment of an end portion of the multi-lumen catheter (B) of the invention in a state where the communication is not shut off with the blood extraction port and the blood return port, and FIG. 17 is a sectional view along the line B-B of the multi-lumen catheter 1 of FIG. 16 on an enlarged scale. FIG. 18 is a side view illustrating, on an enlarged scale, an end portion of the multi-lumen catheter 1 shown in FIG. 16 in a state where communication is shut off with the blood extraction port and the blood return port.

When inserted in the outer tube 4, the inner tube 3 may be inserted in the blood extraction lumen 21 in the outer tube 2 as shown in FIG. 16 or may be inserted in the blood return lumen 31 in the outer tube 2 though not shown. Alternatively, as illustrated in FIGS. 16 to 18, the outer tube 2 may be provided with a lumen 6 for inserting the inner tube separately from the blood extraction lumen 21 and the blood return lumen 31, and the inner tube 4 may be inserted in the lumen 6 for inserting the inner tube. The position of the lumen 6 for inserting the inner tube in the outer tube 2 may be near the central portion along the boundary between the blood extraction lumen 21 and the blood return lumen 31 as shown in FIG. 17, or may be at an end along the boundary. Or, the lumen 6 for inserting the inner tube may be provided in the blood extraction lumen 21 or in the blood return lumen 31 in the outer tube 2. There is no particular limitation on the sectional shape of the lumen 6 for inserting the inner tube. Desirably, the lumen 6 for inserting the inner tube has the same sectional shape as the sectional shape of the inner tube 4, and has an inner diameter slightly larger than the outer diameter of the inner tube 4.

When the dialysis is being carried as shown in FIGS. 11, 12 and 16, the blood extraction lumen 21 of the outer tube 2 communicates with the exterior of the catheter 1 through the blood extraction port 22, and the blood return lumen 31 communicates with the exterior of the catheter 1 through the blood return port 32.

When dialysis is not being carried out, on the other hand, heparin is introduced into the blood extraction lumen 21 and the blood return lumen 31 to establish heparin locking. At this moment as shown in FIGS. 14, 15 and 18, the movable portion 33 is slid toward the base end side relative to the connection portion 23, and the front end of the outer tube 2 is liquid-tightly joined to the base end of the front tip 42, whereby communication with the exterior of the catheter 1 is shut off at the blood extraction port 22 and at the blood return port 32. Even when the catheter 1 is left to stay in the body for an extended period of time, therefore, no blood infiltrates into the blood extraction lumen 21 from the blood extraction port 22 or into the blood return lumen 31 from the blood return port 32, no thrombi are formed, and the heparin locking is reliably maintained.

There is no particular limitation on the shapes of the base end of the front tip 42 and on the front end of the outer tube 2, provided that the communication between the interior and the exterior of the catheter 1 is shut off at the blood extraction port 22 and at the blood return port 32 by the junction thereof. The shape of the base end of the front tip 42 can be suitably changed so as to be liquid-tightly joined to the blood extraction port 22 and the blood return port 32 either when the blood extraction port 22 and the blood return port 32 are formed on a plane at right angles with the long axis of the multi-lumen catheter 1 as shown in FIGS. 12 and 15 or when the blood extraction port 22 and the blood return port 32 are formed on a plane intersecting the long axis of the multi-lumen catheter 1 at an obtuse angle, which is not shown. If the base end of the front tip 42 is formed in a stepped manner such that the blood extraction port 22 and the blood return port 32 are simultaneously joined to the front tip 42 as shown in FIGS. 15 and 18, the sliding distance of the moving portion 33 can be minimized to shut off the communication in the blood extraction port 22 and in the blood return port 32, and the operation becomes easier.

As with the multi-lumen catheter (A) of the invention, the multi-lumen catheter (B) of the invention may be provided with a locking mechanism for securing the connection portion 23 and the movable portion 33 in order to maintain a state where the communication between the interior and the exterior of the catheter 1 is not shut off at the blood extraction port 22 and the blood return port 32, i.e., to hold the outer tube 2 and the inner tube 3 in the arrangement of that when the dialysis is being carried out. The locking mechanism is preferably one based on an engagement of a protuberance formed on the outer surface of the connection portion 23 with a groove formed in the moving portion 33 and extending in the axial direction thereof.

Further, the multi-lumen catheter (B) may be provided with a locking mechanism for securing the connection portion 23 and the moving portion 33 in order to maintain a state where communication between the interior and the exterior of the catheter 1 is shut off at the blood extraction port 22 and at the blood return port 32, i.e., to hold the outer tube 2 and the inner tube 4 in the arrangement of that when the dialysis not being carried out with the front tip 42 of the inner tube 3 being connected to the outer tube 2. The locking mechanism may be the same as the locking mechanism for holding the arrangement of that when dialysis is being carried out.

It is desired that the catheter 1 be provided with both the locking mechanism for maintaining the arrangement of that when dialysis is being carried out and with the locking mechanism for maintaining the arrangement of that when the dialysis is not being carried out. The locking mechanisms in this case are based upon the engagement of the protuberance formed on the outer surface of the connection portion 23 with the groove formed in the moving portion 33 and extending in the axial direction, the groove having a U-shape with its ends bending in a direction perpendicular to the axis, or having a dumbbell shape with wide areas at both ends and with a narrow area at an intermediate portion.

The blood extraction lumen 21 can liquid-communicate with the blood return lumen 31 through the blood extraction port 22 and the blood return port 32 in the state where the outer tube 2 and the front tip 42 are joined together and communication between the interior and the exterior of the catheter 1 at the blood extraction port 22 and at the blood return port 32 is shut off. Therefore, even in case blood remains in either the blood extraction lumen 21 or in the blood return lumen 31 after the introduction of heparin, a liquid such as heparin can be introduced through one lumen and discharged through the other lumen thereby to effectively wash away the blood remaining in the lumens. This constitution makes it possible to safely leave the catheter 1 indwelt in the body of a patient for further extended periods of time.

Next, described below with reference to FIGS. 11 to 15 is how to use the multi-lumen catheter 1 of the invention.

First, as illustrated in FIGS. 14 and 15, the multi-lumen catheter 1 of the invention is introduced into the body of a patient in a state where the front tip 42 of the inner tube 3 is joined to the outer tube 2. To introduce the catheter 1, the base end of a guide wire that has been introduced in the patient in advance by known means is inserted through the opening 43 of the front tip 42 so that the front end of the guide wire remains in a blood vessel and the base end stays outside the body, and the catheter 1 is inserted in the blood vessel along the guide wire. Due to this operation, the base end of the guide wire enters into the movable portion 33 passing through the passage 421 in the front tip 42 and the lumen 41 for inserting the guide wire, and protrudes beyond the connector 334 through the tube 4 for inserting the guide wire. When the catheter 1 is inserted up to a predetermined position, the guide wire in the catheter 1 is pulled out through the connector 334, and the catheter 1 is secured to the body of the patient by using tape or the like. If wings 5 are formed on the surface of the catheter 1, the catheter 1 can be maintained reliably secured for further extended periods of time, which is desirable. The tube 333 for inserting the guide wire is temporarily closed by any suitable means. Heparin may be introduced into tube 333 before it is closed.

Prior to starting the dialysis, the catheter 1 inserted in the blood vessel of the patient is connected to the dialyzer through the connector 232 of the blood extraction tube 231 and the connector 332 of the blood return tube 331. Then, the movable portion 33 is slid toward the front end side relative to the connection portion 23 so as to establish a state as shown in FIGS. 11 and 12. As shown in FIG. 12, the junction is broken between the front tip 42 and the outer tube 2, whereby the blood extraction lumen 21 communicates with the exterior of the catheter 1 through the blood extraction port 22, and the blood return lumen 31 communicates with the exterior of the catheter 1 through the blood return port 32.

After dialysis is started, blood enters into the blood extraction lumen 21 through the blood extraction port 22 and is sent to the dialyzer through the blood extraction tube 231. The blood treated in the dialyzer enters into the blood return lumen 31 through the blood return tube 331, and is returned into the blood vessel through the blood return port 32.

When the dialysis is finished, the connectors 232 and 332 are disconnected from the dialyzer, and the blood extraction lumen 21 and the blood return lumen 31 are filled with heparin. Next, the movable portion 33 is slid toward the base end side relative to the connection portion 23 so as to establish the state shown in FIGS. 14 and 15. As shown in FIG. 18, the front tip 42 and the outer tube 2 are liquid-tightly joined together, and communication with the exterior of the catheter 1 is shut off at the blood extraction port 22 in the blood extraction lumen 21 and at the blood return port 32 in the blood return lumen 31.

In this case, when blood remains in the blood extraction lumen 21 and in the blood return lumen 31, a liquid such as heparin may, as required, be introduced through one lumen and discharged through the other lumen to wash away the blood remaining in these lumens. Thereafter, the blood extraction tube 231 and the blood return tube 331 are closed by any suitable means, and the catheter 1 is left to indwell in the blood vessel until the dialysis is conducted the next time.

When dialysis is conducted repetitively, the movable portion 33 is slid toward the front end side or the base end side relative to the connection portion 23 each time. Parts such as tubes connected to the movable portion 33 and to the connection portion 23 communicate with the blood extraction lumen 21, blood return lumen 31 and lumen 41 for inserting the guide wire. As required, however, members are suitably provided to shut off the communication to prevent the infiltration of bacteria and the leakage of liquid while the catheter is indwelt in the blood vessel.

In the multi-lumen catheter (B) of the invention, means for closing the blood extraction port and the blood return port, which so far has been a sheath provided on the outer side of a catheter, is an outer tube that constitutes the blood extraction lumen and blood return lumen. Therefore, a ratio of the wall portion is not increased in cross section, the diameter of the catheter is not increased and does not give an increased burden to a patient, and the flow rate of the blood is not decreased. Unlike the conventional catheters, further, no gap exists between the catheter and a sheath, and there is no need to design a structure for maintaining liquid tightness in a gap.

In the multi-lumen catheter of the invention, further, the front tip is joined to the outer tube when the dialysis is not being conducted, and the blood extraction lumen and the blood return lumen are shut off from the exterior of the catheter. Accordingly, the blood extraction port and the blood return port are not exposed to blood; i.e., no blood infiltrates into the lumens to form thrombi. Even in a state of being shut off from the exterior, the blood extraction lumen and the blood return lumen communicate with each other inside the catheter through the blood extraction port and the blood return port. Even in a case where blood remains in the lumens, therefore, a liquid such as heparin is introduced from one lumen and is discharged from the other lumen to efficiently wash the two lumens. Accordingly, the blood does not remain in the catheter and heparin locking is reliably maintained making it possible to safely leave the catheter in the blood vessel of the patient for extended periods of time.

In the multi-lumen catheter of the invention, further, communication with the exterior of the catheter is shut off simultaneously in the blood extraction port and in the blood return port due to the junction of the front tip and the outer tube. Therefore, the movable portion needs be slid only over a short distance for shutting the blood extraction lumen and the blood return lumen off from the exterior, and the operation becomes easier.

Additional Embodiment of the Catheters of the Present Invention

An additional embodiment of each of the catheters of the present invention is a multi lumen catheter in which said tube 4 for inserting a guide wire having an inner cavity constituting a lumen 41 for inserting the guide wire and a front tip 42 of a tapered shape further comprises a communication shut-off mechanism 44 capable of shutting off the communication between the lumen 41 for inserting the guide wire and the exterior of the catheter 1.

Mode of Operation

In the multi-lumen catheter of the additional embodiment, the tube for inserting the guide wire is further provided with a communication shut-off mechanism making it possible to reliably prevent the formation of thrombi not only in the blood extraction lumen and the blood return lumen but also in the lumen for inserting the guide wire. The multi lumen catheter of this embodiment is operated in the same manner as the above mentioned multi lumen catheter.

Figure 19:
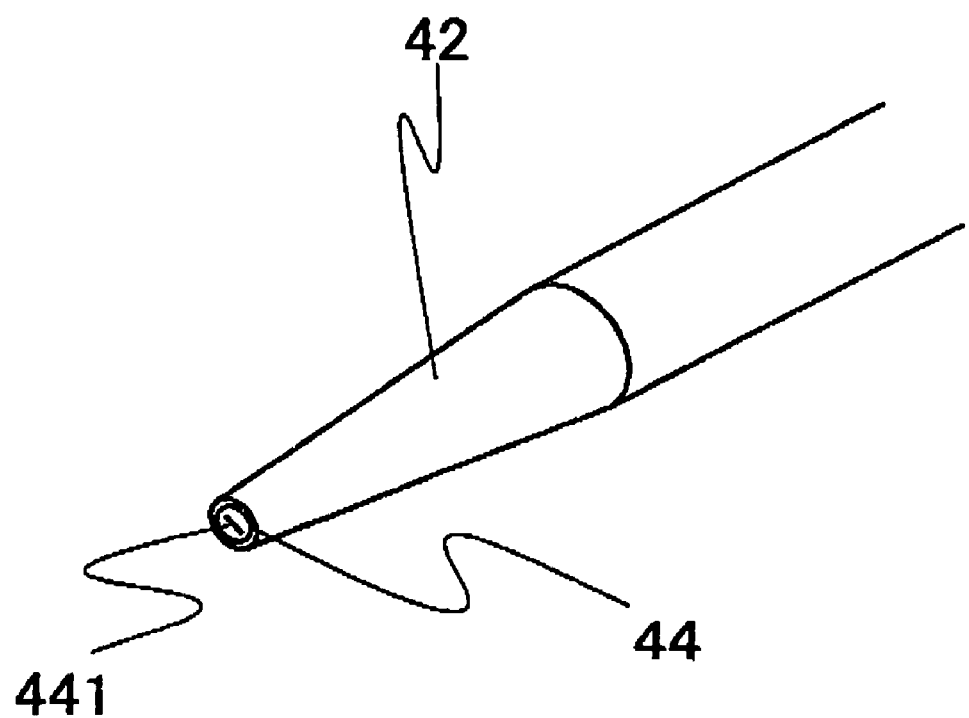
FIG. 19 is a perspective view illustrating, on an enlarged scale, the front end of the multi lumen catheter of FIG. 1.
Figure 20:
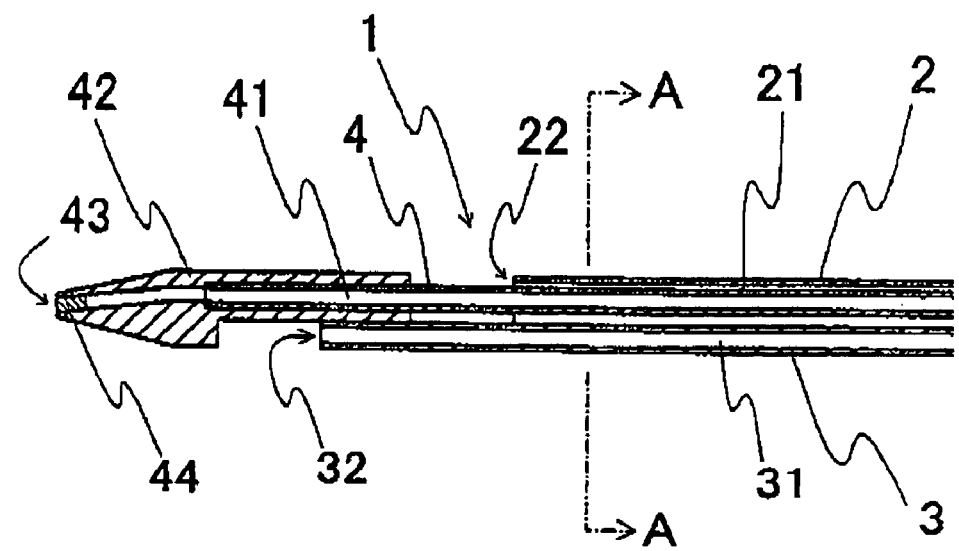
FIG. 20 is a view illustrating, on an enlarged scale, the front end of the multi lumen catheter (B) according to a further embodiment of the invention.
Figure 21:
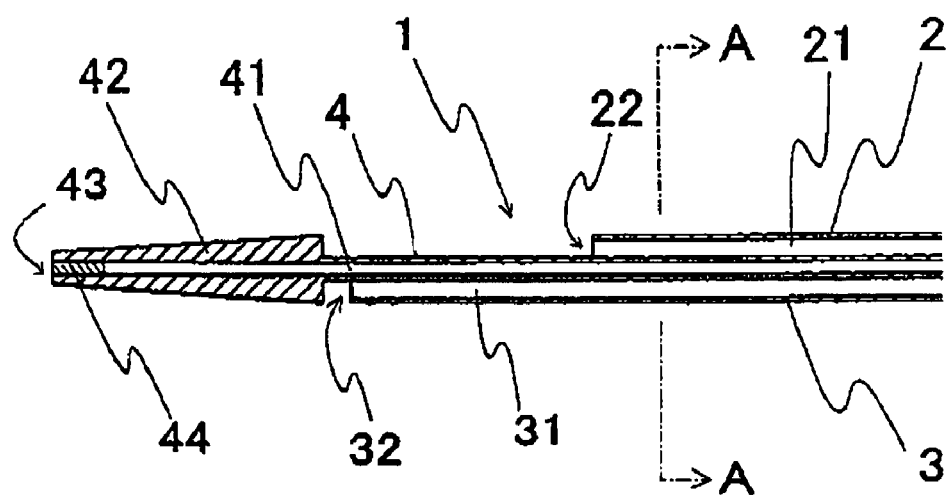
FIG. 21 is a view illustrating, on an enlarged scale, the front end of the multi lumen catheter (B) according to a further embodiment of the invention.

A multi-lumen catheter of the additional embodiment will now be described in detail with reference to catheter (B) as illustrated in FIGS. 19 to 21 of the accompanying drawings. However, the invention is in no way limited to the structures shown in these drawings. The multi lumen catheter (A) illustrated in FIGS. 3 to 9 and the multi-lumen catheter with balloon of the present invention (described below) can also be provided with a communication shut-off mechanism making it possible to reliably prevent the formation of thrombi not only in the blood extraction lumen and the blood return lumen but also in the lumen for inserting the guide wire.

As shown in FIG. 20, the multi-lumen catheter 1 comprises an outer tube 2 having an inner cavity constituting a blood extraction lumen and a blood extraction port at an end; an inner tube 3 having an inner cavity constituting a blood return lumen and a blood return port; and a tube 4 for inserting a guide wire and having an inner cavity constituting a lumen for inserting the guide wire, a front tip 42, and a communication shut-off mechanism 44.

FIGS. 20 and 21 are vertical sectional views illustrating a front end of modified multi-lumen catheters 1 on an enlarged scale.

Referring to FIGS. 20 and 21, the outer tube 2 in the multi-lumen catheter 1 has an inner cavity which constitutes a blood extraction lumen 21. At the front end of the outer tube 2, the blood extraction lumen 21 is fluid-communicated with the exterior of the catheter 1 through blood extraction port 22 which is open toward the front end side in the axial direction of the outer tube 2.

The tube 4 for inserting the guide wire is inserted in the outer tube 2, and its inner cavity constitutes a lumen 41 for inserting a guide wire. A front tip 42 of a tapered shape of which the outer diameter decreases toward the front end side is formed at the front end of the tube 4 for inserting the guide wire. The front tip 42 is a hollow member and its inner cavity communicates with the lumen for inserting the guide wire. Further, the inner cavity of the front tip 42 communicates with the exterior of the catheter 1 through an opening 43 which is open at the front end of the front tip 42 toward the front end side in the axial direction of the inner tube 4 for inserting the guide wire. Near the opening 43, further, there are provided a lumen 41 for inserting the guide wire and a communication shut-off mechanism 44 for shutting off communication between the lumen 41 for inserting the guide wire and the exterior of the catheter 1.

The material constituting the tube 4 for inserting the guide wire and the molding method thereof are preferably the same as those used for outer tube 2 as previously described herein.

When the multi-lumen catheter 1 is left to stay in the patient's body and when the lumen 41 for inserting the guide wire is not being used, the communication shut-off mechanism 44 prevents the infiltration of blood into the lumen 41 for inserting the guide wire so that no thrombi are formed. When the lumen 41 for inserting the guide wire is used, the communication shut-off mechanism 44 works to provide communication between the lumen 41 for inserting the guide wire and the exterior of the catheter 1.

As the communication shut-off mechanism 44, there can be exemplified an elastic member provided with a slit 441 as shown in FIG. 19. The slit 441 in the elastic member easily opens due to the guide wire or a chemical solution introduced into the lumen 41 for introducing the guide wire, but remains liquid-tightly closed when the lumen 41 for inserting the guide wire is not being used.

As the material of the elastic member, there can be exemplified rubbery elastic members such as those made of silicone, synthetic polyisoprene rubber, natural rubber, butyl rubber, chloroprene rubber, urethane rubber, styrene-butadiene rubber, ethylene propylene rubber, acrylic rubber, fluorine-containing rubber, and thermoplastic elastomer. The elastic member is secured to the vicinity of the opening 43 of the lumen 41 for inserting the guide wire by a known method.

There is no particular limitation on the shape of the elastic member provided it is capable of liquid-tightly shutting off the communication between the lumen 41 for inserting the guide wire and the exterior of the catheter 1. Further, the shape of the slit 441 may be a crossing shape or a circular shape in addition to the linear shape shown in FIG. 19.

More desirably, when secured to the lumen 41 for inserting the guide wire, the elastic member has a recessed portion formed on the base end side and, further, has a slit 441 formed in the recessed portion. Owing to this constitution, the guide wire and the chemical solution introduced into the lumen 41 for inserting the guide wire are guided to the exterior of the catheter 1 with a smaller resistance.

When the dialysis is being conducted with the multi-lumen catheter illustrated in FIGS. 19-21 and as previously described in connection with the multi-lumen catheter shown in FIGS. 1, 3 and 6 to 9, the outer tube 2, inner tube 3 and tube 4 for inserting the guide wire are such that the front tip 42, blood return port 32 and blood extraction port 22 are arranged in this order from the front end side. In this state, the blood extraction lumen 21 is communicates with the exterior of the catheter 1 through the blood extraction port 22, and the blood return lumen 31 is communicates with the exterior of the catheter 1 through the blood return port 32.

When the dialysis is not being carried out, on the other hand, heparin is introduced into the blood extraction lumen 21, the blood return lumen 31 and the lumen 41 for inserting the guide wire to establish heparin locking. At this moment as shown in FIGS. 2 and 4, the movable portion 33 is slid toward the base end side relative to the connection portion 23, and the front end of the outer tube 2 is liquid-tightly joined to the base end of the front tip 42, whereby the communication with the exterior of the catheter 1 is shut off in the blood extraction port 31 and in the blood return port 32. Further, the communication of the lumen 41 for inserting the guide wire with the exterior of the catheter 1 is shut off by the communication shut-off mechanism 44. Even when the catheter 1 is left to stay in the body for extended period of time, therefore, no blood infiltrates into the blood extraction lumen 21, blood return lumen 31 or into the lumen 41 for inserting the guide wire, no thrombi are formed, and the heparin locking is reliably maintained.

With the embodiments shown in FIGS. 19 to 21, the lumen 41 for inserting the guide wire is closed by the communication shut-off mechanism 44, and heparin may be introduced into the lumen 41 for inserting the guide wire. At this moment, the tube 341 for inserting the guide wire is closed by any suitable means (see, FIG. 11 or 12).

In the modified embodiment of the multi-lumen catheter of the invention, the tube for inserting the guide wire is further provided with a communication shut-off mechanism making it possible to reliably prevent the formation of thrombi not only in the blood extraction lumen and in the blood return lumen but also in the lumen for inserting the guide wire.

A Multi-lumen Catheter with a Balloon:

Another embodiment of the present invention relates to a multi-lumen catheter with balloon. More specifically, the invention relates to a multi-lumen catheter with balloon comprising an outer cylinder provided on the outermost side of a main tubular catheter body so as to slide in the lengthwise direction of the main body, and thereby to completely shut off the blood in the blood vessel by sliding the outer cylinder without permitting the blood to remain in the blood return port, blood extraction port or in the periphery of the balloon at the time when the blood is not being purified, and preventing the lumen from being clogged by the formation of thrombus.

A so-called single needle blood dialysis method has heretofore been widely employed according to which the blood is sucked while it is being returned by using a double-lumen catheter during the blood dialysis. However, there is a problem of sticking of the blood vessel wall to the blood extraction port at the time of collecting the blood or sucking the blood. Additionally, the single needle blood dialysis method has a particular problem in that dialysis efficiency decreases because the blood before being dialyzed is mixed with the purified blood from the dialysis. In order to solve these problems at one time, the present applicant has proposed a double-lumen catheter with balloon in JP-A-08-131547 (page 2, FIG. 2). According to this proposal, a suitable space is maintained in the blood vessel by a balloon to overcome the problem of sticking, and the blood return port and the blood extraction port are separated from each other with the balloon as a boundary to improve the efficiency of dialysis.

The blood dialysis method is repeated at regular intervals, and the catheter is left to stay in the blood vessel even after the dialysis has been finished and, hence, even while the blood is not being purified (even while the dialysis is not being carried out). In order to avoid the formation of thrombi resulting from blood remaining in the blood extraction lumen and in the blood return lumen, therefore, there is conducted so-called heparin locking by filling the lumens with heparin.

Even when heparin locking is conducted, however, the blood return port and the blood extraction port are still open in the blood vessel, and a complete countermeasure against the formation of thrombi is not realized. Additionally, in the case of the catheter with balloon disclosed in JP-A-08-131547, the balloon portion is secured to the tubular surface of the main catheter body by melt-adhesion or adhesion and there is a problem that such a boundary portion easily serves as a nucleus for forming thrombi.

Furthermore, in the catheter having balloon, the balloon portion has a diameter larger than the diameter of the tube of the main catheter body by a thickness of the balloon even when the balloon is deflated. When the catheter with balloon is inserted in a blood vessel, therefore, the balloon portion easily rubs the wall of the blood vessel. In particular, there is also a problem that an end of the balloon easily scratches the wall of the blood vessel at the boundary portion where the balloon is secured to the tubular surface of the main catheter body.

In order to solve the above problems, according to the present invention, the blood return port, the blood extraction port and the balloon-mounting portion are all closed, except when blood is circulated and purified by using the catheter with balloon and by inflating the balloon at a treating position in the blood vessel, thus enabling the catheter to be smoothly inserted in the blood vessel or pulled out therefrom without damaging the walls of blood vessels. Also, when the catheter is left to stay in a blood vessel, blood is reliably prevented from flowing into the blood return port or the blood extraction port, and the blood is reliably prevented from adhering onto the balloon portion so as to prevent the formation of thrombi and, hence, so as to realize perfect heparin locking.

Namely, a further embodiment of the present invention is a multi lumen catheter (C) with balloon comprising:

a base end portion (51);

a slender flexible tubular main body (52) extending from the base end portion (51) to a front end portion;

a front tip (53) having an outer shape that tapers toward the front end which is provided at a front end of the tubular main body (52);

a balloon (12) provided on an outer side of the tubular main body (52) at a portion close to the front tip side but on the side of the base end portion (51), and having an outer diameter, when deflated, smaller than a maximum outer diameter of the front tip (53);

either one of a blood return port (81) of a blood return lumen (13) and a blood extraction port (61) of a blood extraction lumen (14) being formed in the tubular main body (52) on the side of the front tip (53) in front of the balloon (12) and the other being formed in the tubular main body (52) on the side of the base end portion (51) in back of the balloon (12); and an outer tube (50) provided on the outermost side of said tubular main body (52) so as to slide in the lengthwise direction of said body (52), wherein the blood extraction port (61), the blood return port (81) and a balloon-mounting portion are closed when the end of the outer tuber (50) comes in contact with the front tip (53).

According to the present invention, when the blood is to be purified (dialyzed) while being circulated, the blood return port of the blood return lumen and the blood extraction port of the blood extraction lumen are arranged on the front tip side and on the base end portion side of the balloon with the inflated balloon as a boundary, whereby dialysis therapy is efficiently conducted without permitting the blood before the dialysis to be mixed with the purified blood after the dialysis. Further, the front tip has an outer shape that tapers toward the front end, and the balloon when deflated, has an outer diameter smaller than a maximum outer diameter of the front tip and is closed by sliding of the outer tube. Therefore, the multi-lumen catheter with balloon of the invention can be easily inserted in a blood vessel and can also be easily pulled out therefrom. Even when the multi-lumen catheter with balloon of the invention rubs the wall of the blood vessel, therefore, the wall of the blood vessel does not get scarred easily since the catheter has no protrusion such as an edge of the balloon. Further, when the end of the outer tube is slid and comes in contact with the front tip, then, the balloon which is deflated, the blood return port and the blood extraction port are all closed to maintain liquid-tightness to a sufficient degree despite a simple structure of the catheter. When the catheter is left to indwell in the blood vessel, therefore, the blood is reliably prevented from flowing into the blood return port or into the blood extraction port, the blood is reliably prevented from adhering onto the balloon portion thus preventing the formation of thrombi, and perfect heparin locking is accomplished.

In the multi-lumen catheter with balloon of the invention, further, the outer tube which operates to close all of the deflated balloon, the blood return port and the blood extraction port, also serves as an outer wall of the blood extraction lumen, and closes the catheter to the exterior when it is slid in the lengthwise direction of the main catheter body. In this case, the total diameter of the catheter is smaller than that of the case when a dedicated sheath is used for opening and closing a catheter, thereby decreasing a burden to a patient. Further, in one embodiment means for collecting the blood from the blood extraction port of the blood extraction lumen is formed throughout the whole circumference at the end of the outer cylinder, whereby the blood flows uniformly, unlike the case when the means is a local round port. Accordingly, a sufficient flow rate of the blood is maintained despite the fact that the catheter has a small diameter, which is desirable. Further, when the blood return lumen also serves as a lumen for a guide wire, cross sectional area can be further decreased, and the diameter of the catheter can be further decreased.

Embodiments of the invention will now be described in detail with reference to FIGS. 22 to 26 of the drawings.

A multi-lumen catheter 1' with balloon of FIG. 22(a) includes a base end portion (51), a slender and flexible tubular main body (52) extending from the base end portion (51) toward a front end portion, and a front tip (53) nearly conical in shape and having an outer diameter that decreases toward the front end side. A balloon (12) is provided close to the front tip (53) but on the side of the base end portion (51) of the front tip (53). A blood return port (81) of a blood return lumen (14) (described later) and a blood extraction port (71) of a blood extraction lumen (13) (described later) are so provided that either one of them is located on one side of the front tip (53) in front of the balloon (12) and the other one is located on the other side of the base end portion (51) at the back of the balloon (12).

As used herein, the front end stands for the side (left side in the drawing) that is inserted in the body of a patient, and the base end stands for the side (right side in the drawing) where connectors, the dialyzer and the like are provided outside the body of the patient.

Here, the front tip (53) is secured to an end of a tubular wall that constitutes at least one or more lumens for extracting the blood, for returning the blood, for a guide wire and for a balloon, constituting the multi-lumen catheter of the invention. As the outermost side of the tubular main body (52), there is provided an outer tube (50) in the lengthwise direction capable of sliding relative to the tubular wall of the lumen supporting the front tip (53) In the deflated state, the balloon (12) has an outer diameter smaller than the inner diameter of the outer tube (50), and serves as a lumen for constituting the inner portion of the catheter in a state of being communicated with a lumen through which a pressurized fluid is introduced into the balloon (12), or is constituted integrally with the other lumen of the inner portion enabling the blood return port (81), the blood extraction port (71) and the portion for mounting the balloon (12) (deflated) to be closed as the outer cylinder (50) is closed (refer to FIGS. 22(b) and (c)). FIG. 22(d) illustrates balloon (12) as inflated during the dialysis therapy.

In FIG. 22(a), the base end portion (51) includes connectors for balloon (12), for removing the blood (43), for returning the blood (83), and for the guide wire (93), that are connected to the blood dialyzer and to related equipment (not shown), as well as conduits (62), (72), (82), (92) thereof, and a connection portion (16) where the conduits converge so as to communicate with the lumens that will be described below in detail. The connection portion (16) further includes a mechanism (not shown) for sliding the outer tube (50) relative to the lumens that constitute the inner side of the catheter described above as shown in FIGS. 22(b) and (c). A fixed wing (17) is provided at the root of the connection portion (16) on the side of the main body (52) or near a portion where the main body (52) is coupled to the connection portion (16). This portion is stuck to the surface of the patient's skin using tape to prevent the catheter from being deviated or removed even when dialysis therapy is conducted for extended periods of time.

A lumen (15) for a guide wire (described later) extends from the connector (93) for the guide wire in the base end portion (51) of FIG. 22(a) up to a front end port (91) of the front tip (53) passing through the conduit (92), connection portion (16) and nearly the central portion of the tube of the main body (52). When it is attempted to insert the catheter in the blood vessel of a patient, an end of the guide wire that has been introduced in the patient's blood vessel in advance is inserted through the front end port (91) of the front tip (53), and the catheter is introduced into the blood vessel from the front end side thereof along the guide wire.

Embodiments of the catheter with balloon will now be described in detail with reference to FIGS. 23 to 26 which illustrate major portions of the catheter of the invention.

Figure 23:
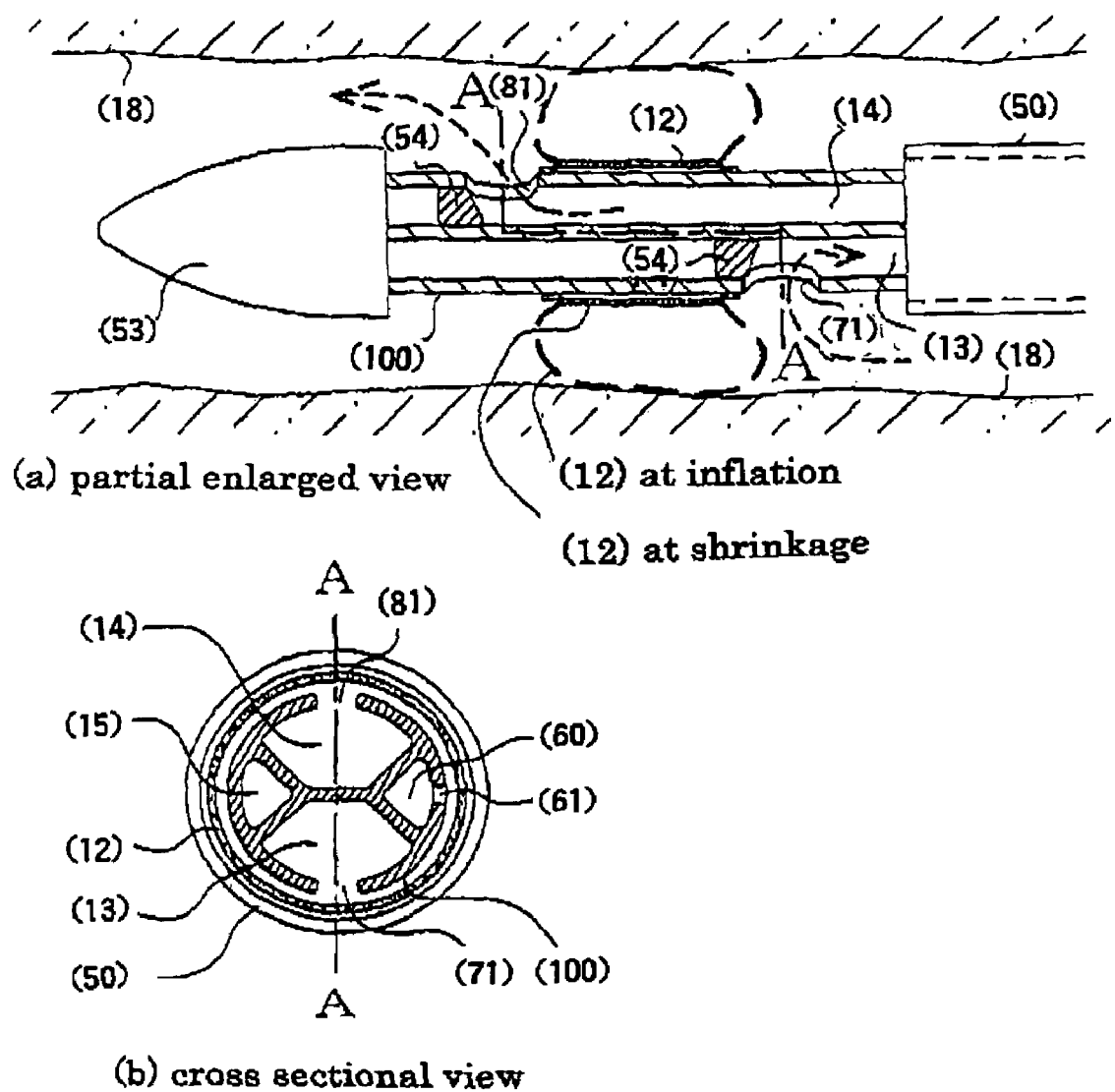
FIGS. 23(a) and (b) are views illustrating, on an enlarged scale, major portions of another embodiment of the multi lumen catheter with balloon of the invention with (a) being a partial enlarged view and (b) being a cross sectional view.

FIG. 23 [where (a) is a partial sectional view and (b) is a sectional view along line A-A] illustrates an embodiment of the multi lumen catheter with balloon of the invention in a state where the outer tube (50) has been slid toward the side of the base end portion (51) of the catheter to start dialysis of the blood by inflating the balloon (12). In FIG. 23(b), the blood extraction lumen (13), blood return lumen (14), lumen (15) for the guide wire and lumen (60) for the balloon, constituting the catheter, are formed in an inner tube (100) being partitioned by the walls, and the front tip (53) is secured to an end of the inner tube (100).

After the blood is dialyzed, the outer cylinder (50) is slid toward the front tip (53) and the end of the outer cylinder is brought into contact with the front tip (53) to thereby close all of the deflated balloon (12), the blood return port (81) and the blood extraction port (71). When the outer diameter of the outer tube (50) is of the same size as the maximum outer diameter of the front tip (53), the end of the outer tube (50) is press-contacted to the edge of the bottom surface of the conically shaped front tip (53) on the side opposite to the front end of the front tip (53) to thereby maintain liquid-tightness between the two. When the inner diameter of the outer tube (50) is nearly the same as, or is slightly smaller than, the maximum outer diameter of the front tip (53), the edge of the bottom surface of the front tip (53) on the side opposite to the front end functions to cover the end of the outer tube (50) to maintain liquid-tightness between the two.

During dialysis, the catheter is introduced into the blood vessel with its front tip (53) being directed in the direction of flow of the blood. The blood extraction port (71) and the blood return port (81) are open in the respective tubular walls of the blood extraction lumen (13) and of the blood return lumen (14), whereby the interior of the blood vessel communicates with the lumens, the blood introduced through the blood extraction port (71) is purified by passage through the blood dialyzer, and is returned back into the blood vessel through the blood return port (81), thereby purifying the blood while circulating it. Sealing members (54) are inserted in front of the blood extraction port (71) and the blood return port (81) of the blood extraction lumen (13) and of the blood return lumen (14), so that the blood will not flow in these lumens toward the front end side. However, sealing may be accomplished by solidly molding the front end portions of the lumens.

As described above, between the blood extraction port (71) and the blood return port (81), there is provided a balloon (12) of which an end portion is secured by adhesion (or by melt adhesion) to the outer wall of the inner tube (100). The balloon (12) has a gap in the central portion thereof and is capable of being inflated to the outer side beyond the outer wall of the tube. When inflated, the balloon (12) reaches the blood vessel wall (18) as indicated by a broken line in FIGS. 23 and 24 to shut off the flow of blood. Therefore, the dialysis treatment is efficiently conducted without permitting the blood prior to the dialysis to be mixed with the purified blood after the dialysis. In a deflated state, the balloon (12) has an outer diameter which is smaller than the inner diameter of the outer tube (50). Referring to FIG.

23(b), the inner tube (100) of the catheter tube is provided with a balloon lumen (60) for flowing a gas or a liquid (pressurized fluid) for inflating and deflating the balloon (12). The pressurized fluid such as air or heparin-added physiological saline solution is sent from a pressurized fluid feeding device (not shown) into the gap (between the balloon (12) and the outer wall of the inner tube (100) through a balloon opening port (61), and the balloon (12) is inflated or deflated. The balloon is inflated roughly 2 to 3 times its cylindrical diameter, and is preferably made of a resin having excellent expanding/contracting properties and a hardness that does not scratch the blood vessel walls, such as polyurethane, silicone resin, ethylene/vinyl acetate copolymer, olefin copolymer, cross-linked ethylene/vinyl acetate copolymer, styrene/butadiene rubber, polyamide elastomer, polyisoprene rubber or soft vinyl chloride resin.

The outer cylinder (50) and the inner tube (100) are preferably formed by extrusion-molding a resin having both flexibility and tensile strength, such as polyurethane, polyethylene, polypropylene, polyamide, polyester, a fluorine-containing resin or silicone resin. The front tip (53) can be formed by injection-molding the same material as used for the outer cylinder (50) and the inner tube (100), or can be formed by injection-molding a synthetic rubber material having rubbery elasticity since it must maintain liquid-tightness at a portion where it comes in contact with an end of the outer cylinder (50).

The main catheter body (52) must be long enough to be indwelt from the skin of the patient to a blood vessel, and is selected to be, for example, from about 100 to about 300 mm in length. The sizes of the outer cylinder (50) and of the inner tube (100) are suitably determined to be as small as possible to minimize the pain caused to a patient and within a range of maintaining a sufficient strength against kinking and rupture while taking into consideration the materials used, flow rates of blood in the respective lumens, flow rate of the pressurized fluid for the balloon and the size of the guide wire. For example, the inner tube (100) preferably is designed to have an outer diameter of from 3 to 5 mm and a thickness of from about 0.2 to about 0.5 mm, and the outer tube (50) is designed to have an inner diameter which is larger than the outer diameter of the inner tube 100 by about 0.1 to about 0.3 mm.

When deflated, the balloon (12) has a length of from about 5 to about 20 mm (inflating/deflating portion excluding 2 to 3 mm of fixing portions) as calculated back from an inflation of about 2 to 3 times the cylindrical diameter. It is desired that the blood extraction port (71) and the blood return port (81) are each arranged relative to the balloon (12) within a range of about 2 to 20 mm from the ends of the balloon (12). When the distance is smaller than 2 mm, the opening is so close to the side surface of the balloon (12) that the blood tends to remain. When the distance exceeds 20 mm, on the other hand, there easily occurs a so-called sticking phenomenon in which the blood extraction port and tube in the vicinity thereof stick to the blood vessel, which is not desirable. It is desired that the thickness of the balloon (12) (when deflated) is roughly from 0.1 to 0.1 mm though it may differ slightly depending upon the material that is used. When the thickness is smaller than the above range, the tolerance in the thickness results in deformation accompanying inflation, and a uniformly expanded shape is not obtained. When the thickness is larger than the above range, the thickness remains large after deflation. Additionally, extra output is required for providing the pressurized fluid and it becomes difficult to finely control the magnification of inflation, which is also not desirable.

Figure 24:
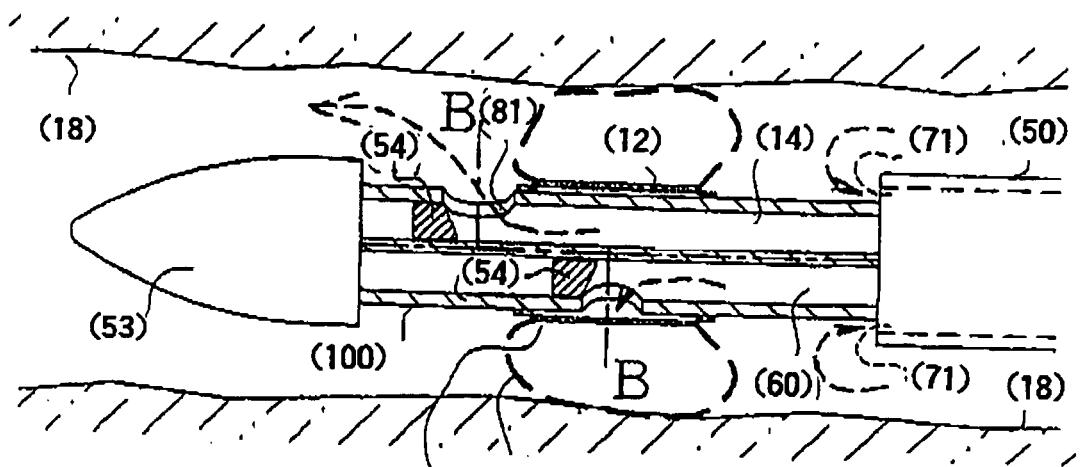
FIGS. 24(a) and (b) are views illustrating, on an enlarged scale, major portions of FIG. 22 with (a) being a partial enlarged view and (b) being a cross sectional view.
Figure 24:
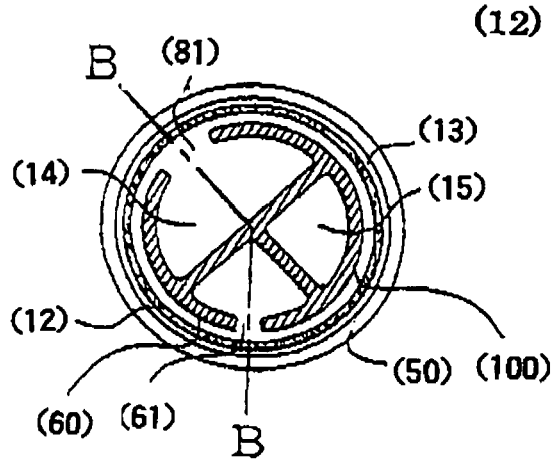

FIG. 24 is a view [where (a) is a partial sectional view and (b) is a sectional view along line A-A] illustrating, on an enlarged scale, portions of the embodiment of the multi-lumen catheter with balloon of the invention shown in FIG. 22(a). The basic structure for dialyzing the blood is the same as that of FIGS. 23(a) and (b) described above. Here, however, what makes this embodiment different from the constitution of FIGS. 23(a) and (b) is that the outer tube (50) for closing all portions of the balloon (12) that is deflated, the blood extraction port (71) and the blood return port (14), also serves as an outer wall for the blood extraction lumen. Referring to FIG. 24(b), the blood extraction lumen (13) is formed over the whole circumference of the outer wall of the inner tube (100) just inside the outer tube (50).

The inner tube (100) is the same as that of FIGS. 23(a) and (b) in regard to the contact between the front tip (53) and the outer tube (50), and to the inflation/deflation of the balloon (12), except that the blood return lumen (14), lumen (15) for the guide wire and lumen (60) for balloon, other than the blood extraction lumen (13), are constituted in a tubular shape being partitioned by walls. Therefore, the inner tube (100) is not described here.

In this embodiment, the whole diameter can be further decreased as compared with that of a catheter having an opening/closing sheath, and the burden to the patient can be desirably further decreased. Additionally, means for collecting the blood from the blood extraction port (71) is formed throughout the whole circumference of the inner wall at the end of the outer tuber (50), whereby the blood flows uniformly unlike the case of a localized shape such as a round port. Accordingly, the phenomenon of sticking of the catheter to the blood vessel occurs more rarely, the balloon needs be inflated to a degree just for simply shutting off the flow of blood, and a sufficient flow rate of the blood is maintained despite the tube being of a small diameter even from the standpoint of maintaining the flow rate of the blood being removed, which is desirable.

Figure 25:
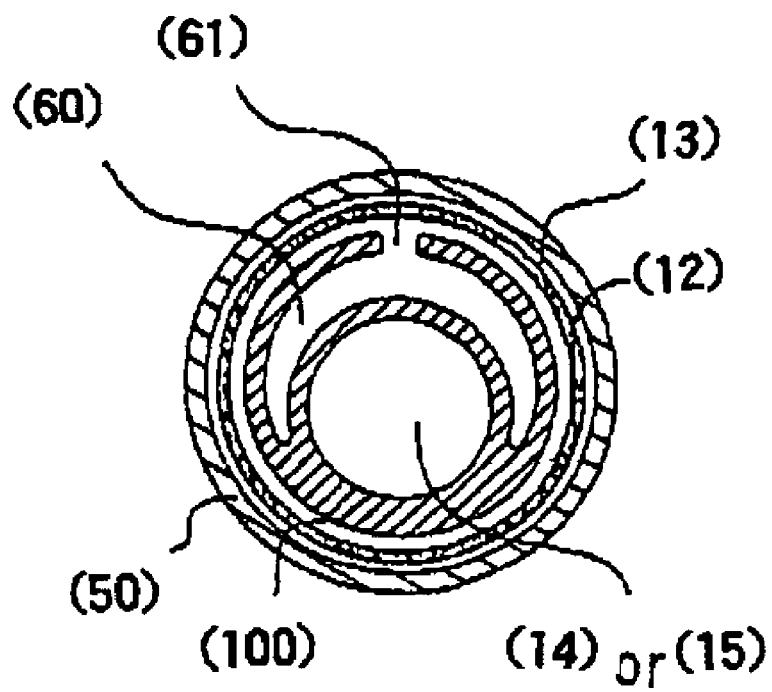
FIG. 25 is a cross sectional view illustrating major portions of another embodiment of the multi lumen catheter with balloon of the invention.

Or, as shown in FIG. 25, the blood return lumen (14) may also be used as the lumen (15) for the guide wire. In this case, area is further decreased in the inner cylinder (100) in cross section, and the diameter of the catheter can be further decreased, which is useful.

Figure 26:
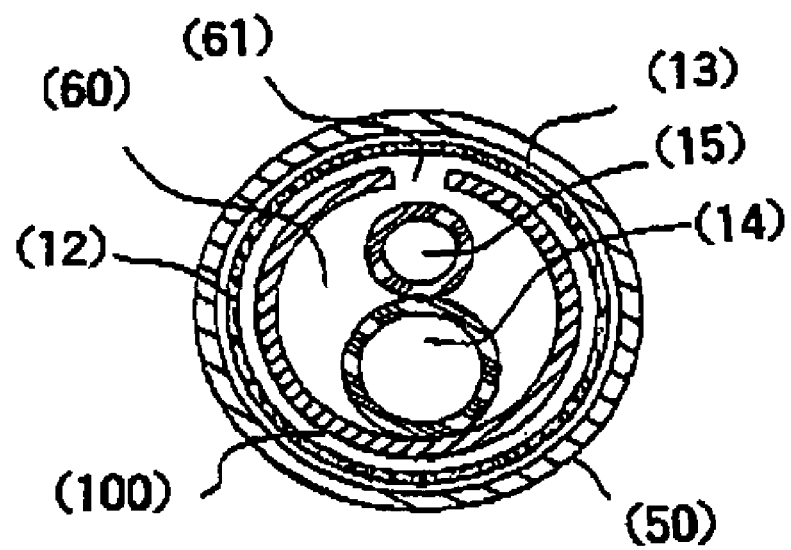
FIG. 26 is a cross sectional view illustrating major portions of a further embodiment of the multi lumen catheter with balloon of the invention.

In the foregoing description, the plurality of lumens constituting the inner tube (100) are in a tubular form being partitioned by walls in the tube. This invention, however, is in no way limited thereto and the plurality of lumens may be constituted by a plurality of tubes as shown in FIG. 26 or may be, further, constituted by forming concentric cylindrical tubular walls so that the gaps among the tubular walls serve as respective lumens.

As with catheters (A) and (B), the multi-lumen catheter with balloon of the invention can be provided with a communication shut-off mechanism to prevent the formation of thrombi in the lumen for inserting the guide wire.

Figure 22:
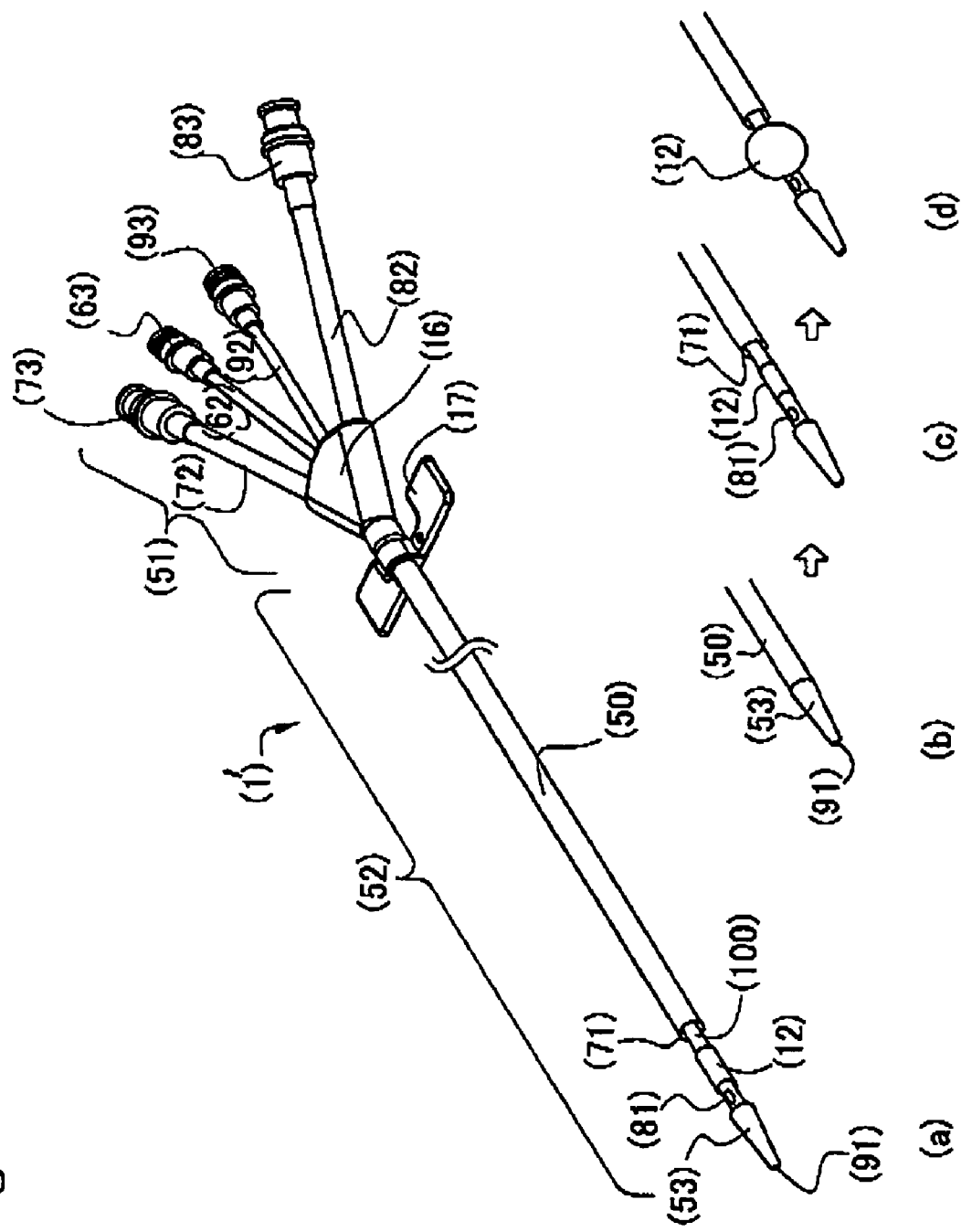
FIGS. 22(a), (b), (c) and (d) are perspective views illustrating the appearance of an embodiment of a multi lumen catheter with balloon of the invention.

Next, described below with reference to FIGS. 22 to 24 is how to use the multi-lumen catheter (1') with balloon of the invention.

First, the multi-lumen catheter (1') with balloon of the invention is introduced into the body of the patient in a state [FIG. 22(b)] where the end of the outer cylinder (50) is in contact with the bottom surface of the substantially conically shaped front tip (53) (i.e., the bottom of the cone) secured to the front end of the inner tube (100) on the side opposite to the front end of the front tip (53). To introduce the catheter (1'), the base end of a guide wire that has been introduced into a blood vessel of a patient in advance by known means is inserted through the front end port (91) of the front tip (53)

so that the front end is retained in the blood vessel and the base end stays outside the body and the catheter (1') is introduced from its front end side into the blood vessel of the patient along the guide wire. Due to this operation, the base end of the guide wire runs through the guide wire lumen (15) and through the connection portion (16), and protrudes toward the connector (93) from the conduit (92). When the catheter (1') is inserted up to a predetermined position along the guide wire, the guide wire in the catheter (1') is pulled out through the connector (93), and the catheter (1') is secured by a fixing wing (17) to the body of the patient by using medical tape.

Prior to starting the dialysis, the catheter (1') inserted in the blood vessel of the patient is connected to the dialyzer through the connector (73) of the blood extraction tube (72) and the connector (83) of the blood return tube (82). Then, the connector (63) of the tube (62) for balloon is connected to a balloon fluid feeding device. Next, as shown in FIGS. 22(*b*) and (*c*), the outer cylinder (50) is slid toward the side of the base end portion (51). Here, the outer tube (50) and the inner tube (100) may be slid relative to each other. Depending upon the mechanism, the inner tube (100) may slide together with the front tip (53) in the direction of the front end of the catheter (1'). The blood extraction lumen (13) provides communication of the blood vessel with the dialyzer through the blood extraction port (81), connection portion (16), conduit (72) and connector (73), and the blood after being purified is sent from the dialyzer back into the blood vessel through the blood return connector (83), conduit (82), connection portion (16), blood return lumen (14) and blood return port (81), thereby to start the dialysis. Then, after the start of dialysis, the pressurized fluid is sent from the balloon fluid feeding device through the balloon connector (63), conduit (62) and lumen (60) for balloon until a predetermined magnification of inflation is reached, and the balloon (12) becomes inflated as shown in FIG. 22(*d*).

In order to avoid an occurrence in which air is present in the dialyzing circuit and is sent into the patient's blood vessel, it is necessary to take a suitable measure such as filling the circuit with a heparin-added physiological saline solution prior to starting the dialysis, or similarly sending the heparin-added physiological saline solution into the lumen (15) for guide wire after the guide wire has been pulled out and then sealing the connector (93) with a plug.

After the dialysis has been finished, the pressurized fluid is returned back to the balloon fluid feeding device to deflate the balloon (12). Then, after the connector (73) and the connector (83) are removed from the dialyzer, the blood extraction lumen (13) and the blood return lumen (14) are filled with the heparin-added physiological saline solution. Then, outer tube (50) is slid toward the front tip (53) to bring the end of the outer tube (50) into contact with the front tip (53) thereby to liquid-tightly close all of the deflated balloon (12), the blood return port (81) and the blood extraction port (71).

Advantage of the Invention

As described above in detail, the multi-lumen catheter with balloon of the invention comprises a base end portion; a slender flexible tubular main body extending from the base end portion to a front end portion; and a front tip having an outer shape that tapers toward the front end; wherein a balloon is provided at a portion close to the front tip but on the side of the base end portion, the balloon having an outer diameter when it is deflated that is smaller than a maximum outer diameter of the front tip. Either one of a blood return port of a blood return lumen or a blood extraction port of a blood extraction lumen is formed on the front tip side the balloon and the other one is formed on the base end portion side of the balloon, an outer tube is provided on the outermost side of the tubular main body so as to be capable of sliding in the lengthwise direction of the body, and the blood return port, the blood extraction port and a balloon-mounting portion are closed when the end of the outer cylinder comes in contact with the front tip. Therefore, the blood return port of the blood return lumen and the blood extraction port of the blood extraction lumen are arranged on the front tip side and on the base end portion side of the balloon with the inflated balloon as a boundary, whereby dialysis therapy can be efficiently conducted without permitting the blood before the dialysis to be mixed with the purified blood after the dialysis. Further, the front tip has an outer shape that tapers toward the front end, and the balloon when deflated has an outer diameter smaller than a maximum outer diameter of the front tip. Therefore, the multi-lumen catheter with balloon can be easily inserted in a blood vessel and can be easily pulled out therefrom. Even when the multi-lumen catheter with balloon rubs the wall of a blood vessel, therefore, the wall of the blood vessel does not get easily scarred. Further, as the end of the outer tube is slid and brought into contact with the front tip, then, the balloon which is deflated, the blood return port and the blood extraction port are all closed to maintain liquid-tightness to a sufficient degree despite a simple structure. When the catheter is left to stay in the blood vessel, therefore, the blood is reliably prevented from flowing into the blood return port or into the blood extraction port, the blood is reliably prevented from adhering onto the balloon portion thereby preventing the formation of thrombi, and a perfect heparin locking is accomplished.

In the multi-lumen catheter with balloon of the invention, further, the outer tube which works to close all of the deflated balloon, the blood return port and the blood extraction port to the exterior, also serves as an outer wall of the blood extraction lumen. In this case, the total diameter is decreased, and a smaller burden is given to a patient as compared to a catheter with a sheath, which is desirable. Further, in one embodiment means for collecting the blood from the blood extraction port of the blood extraction lumen is formed throughout the whole circumference at the end of the outer tube, whereby the blood is extracted uniformly, unlike the case of a localized round port. Accordingly, a sufficient flow rate of the blood is maintained despite the use of a catheter of a small diameter, which is further desirable. When the blood return lumen also serves as a lumen for a guide wire, further, cross-sectional area can be further decreased, and the diameter of the catheter can be further decreased.

What is claimed is:

1. A multi lumen catheter comprising:
   an outer tube having an inner cavity constituting a blood extraction lumen, and a blood extraction port which is open at an end facing the front end side in the axial direction and communicates said blood extraction lumen with the exterior of the catheter;
   an inner tube having (a) an inner cavity constituting a blood return lumen and (b) a blood return port for communicating said blood return lumen with the exterior of the catheter; and
   a guide wire tube for inserting a guide wire and having (a) an inner cavity constituting a lumen for inserting the guide wire, and (b) a front tip of a tapered shape;
   wherein said blood extraction lumen is defined by an inner surface of said outer tube and outer surfaces of said inner tube and said guide wire tube, and wherein said inner tube and guide wire tube are inserted in said outer tube, and are allowed to slide relative to said outer tube, and the front tip slides with said guide wire tube between a first open position and a second closed position and in said second closed position the tip is joined to the front end of said outer tube to shut off communication of said blood extraction lumen and said blood return lumen from the exterior of the catheter.

2. A multi lumen catheter comprising:

an outer tube having a front end and a base end, an inner cavity constituting a blood extraction lumen, and a blood extraction port which is open at an end facing the front end side in the axial direction and communicates said blood extraction lumen with the exterior of the catheter;

an inner tube having an inner cavity constituting a blood return lumen and a blood return port for communicating said blood return lumen with the exterior of the catheter; and a guide wire tube for inserting a guide wire and having (a) an inner cavity constituting a lumen for inserting the guide wire, and (b) a front tip of a tapered shape;

wherein said blood extraction lumen is defined by an inner surface of said outer tube and outer surfaces of said inner tube and said guide wire tube, and wherein said inner tube is at least partly secured to said guide wire tube for inserting the guide wire, said inner tube and said guide wire tube for inserting the guide wire are inserted in said outer tube and are slidable relative to said outer tube between a first open position and a second closed position such that, in said first open position, said outer tube, said inner tube and said guide wire tube for inserting the guide wire are in such an order that the front tip, the blood return port and the blood extraction port are successively arranged in order from the front end side, and the blood extraction lumen with the blood extraction port and the blood return lumen with the blood return port communicate with the exterior of the catheter, and, in said second closed position, the front tip of said guide wire tube for inserting the guide wire is joined to the front end of said outer tube, and the communication of said blood extraction lumen and said blood return lumen from the exterior of the catheter is shut off.

3. The multi lumen catheter according to claim 2, wherein the blood extraction lumen in the blood extraction port and the blood return lumen in the blood return port communicate with the exterior of the catheter in said first open position when the dialysis as being conducted, and the communication of said blood extraction port and said blood return port from the exterior of the catheter is shut off in said second closed position when the dialysis is not being conducted.

4. The multi lumen catheter according to claim 2, wherein said inner tube and said guide wire tube for inserting the guide wire are independent from each other.

5. The multi lumen catheter according to claim 2, wherein said inner tube and said guide wire tube for inserting the guide wire share a wall over the full length of said inner tube.

6. The multi lumen catheter according to claim 2, wherein said guide wire tube for inserting the guide wire is inserted in said inner tube.

7. The multi lumen catheter according to claim 2, wherein said inner tube and said guide wire tube for inserting the guide wire are secured to each other at base end portions thereof.

8. The multi lumen catheter according to claim 2, wherein said inner tube is secured at its front end to the front tip of said guide wire tube for inserting the guide wire.

9. The multi lumen catheter according to claim 2, wherein said blood return port in said inner tube is open at an end facing the front end side in the axial direction.

10. The multi lumen catheter according to claim 2, wherein said blood return port in said inner tube is a side port opening in the side surface of said inner tube.

11. The multi lumen catheter according to claim 2, further comprising a locking mechanism for locking the arrangement of the outer tube, inner tube and guide wire tube for inserting the guide wire in said first open position.

12. The multi lumen catheter according to claim 2, further comprising a locking mechanism for locking the jointing of the front tip of said guide wire tube for inserting the guide wire and said outer tube in said second closed position.

13. The multi lumen catheter according to claim 2, wherein said guide wire tube for inserting a guide wire having an inner cavity constituting a lumen for inserting the guide wire and a front tip of a tapered shape further comprises a communication shut-off mechanism capable of shutting off communication between the lumen for inserting the guide wire and the exterior of the catheter.

14. A multi lumen catheter according to claim 13, wherein said inner tube and said outer tube share a wall.

15. A multi lumen catheter according to claim 13, wherein said guide wire tube for inserting the guide wire is inserted in the blood extraction lumen of said outer tube.

16. A multi lumen catheter according to claim 13, wherein said guide wire tube for inserting the guide wire is inserted in said inner tube.

17. A multi lumen catheter according to a claim 13, wherein the inner cavity of said outer tube is further provided with a lumen in which can be inserted said guide wire tube for inserting the guide wire.

18. A multi lumen catheter according to claim 13, wherein said blood return port in said inner tube is a side port opening in the side surface of said inner tube.

19. A multi lumen catheter according to claim 13, wherein said blood return port of said inner tube is open at an end facing the front end side in the axial direction.

20. A multi lumen catheter according to claim 13, wherein the joint between said front tip and said outer tube is formed on a plane that meets the long axis of said multi lumen catheter at right angles.

21. A multi lumen catheter according to claim 13, wherein the joint between said front tip and said outer tube is formed on a plane that meets the long axis of said multi lumen catheter at an obtuse angle.

22. A multi lumen catheter according to claim 13, further comprising a locking mechanism for holding said outer tube, said inner tube and said guide wire tube for inserting the guide wire in said first open position where communication has not been shut off in said blood extraction port and in said blood return port.

23. A multi lumen catheter according to claim 13, further comprising a locking mechanism for holding said outer tube, said inner tube and said guide wire tube for inserting the guide wire in said second closed position where communication has been shut off in said blood extraction port and in said blood return port.

* * * * *

UNITED STATES PATENT AND TRADEMARK OFFICE
CERTIFICATE OF CORRECTION

| | | |
|---|---|---|
| PATENT NO. | : 7,282,041 B2 | Page 1 of 1 |
| APPLICATION NO. | : 10/606374 | |
| DATED | : October 16, 2007 | |
| INVENTOR(S) | : Junichi Igarashi et al. | |

It is certified that error appears in the above-identified patent and that said Letters Patent is hereby corrected as shown below:

Title page, item [75], inventors: add -- Akio Kawamura, Motoki Yonekawa and Kazutaka Kukita --

Signed and Sealed this

Eighteenth Day of November, 2008

JON W. DUDAS
*Director of the United States Patent and Trademark Office*